(12) United States Patent  (10) Patent No.: US 9,134,317 B2
Kleinfeld et al.  (45) Date of Patent: Sep. 15, 2015

(54) DEVELOPMENT AND USE OF CYSTEINE-LABELED FLUORESCENT PROBES OF UNBOUND ANALYTES

(75) Inventors: Alan Marc Kleinfeld, La Jolla, CA (US); Andrew Henry Huber, Encinitas, CA (US); James Patrick Kampf, San Diego, CA (US); Thomas Kwan, San Diego, CA (US); Baolong Zhu, San Diego, CA (US)

(73) Assignee: Alan Kleinfeld, La Jolla, CA (US)

( * ) Notice: Subject to any disclaimer, the term of this patent is extended or adjusted under 35 U.S.C. 154(b) by 631 days.

(21) Appl. No.: 12/810,505

(22) PCT Filed: Jan. 16, 2009

(86) PCT No.: PCT/US2009/031341
§ 371 (c)(1),
(2), (4) Date: Jun. 24, 2010

(87) PCT Pub. No.: WO2009/092047
PCT Pub. Date: Jul. 23, 2009

(65) Prior Publication Data
US 2010/0298162 A1   Nov. 25, 2010

Related U.S. Application Data

(60) Provisional application No. 61/022,261, filed on Jan. 18, 2008.

(51) Int. Cl.
*C40B 30/04*  (2006.01)
*G01N 33/68*  (2006.01)

(52) U.S. Cl.
CPC .............. *G01N 33/68* (2013.01); *C40B 30/04* (2013.01)

(58) Field of Classification Search
None
See application file for complete search history.

(56) References Cited

U.S. PATENT DOCUMENTS

| 5,470,714 | A | 11/1995 | Kleinfeld |
| 6,083,708 | A | 7/2000 | Singh et al. |
| 6,444,432 | B1 | 9/2002 | Kleinfeld |
| 6,552,170 | B1 | 4/2003 | Thompson et al. |
| 2002/0013003 | A1* | 1/2002 | Wagner et al. ............... 436/518 |

(Continued)

FOREIGN PATENT DOCUMENTS

WO   WO 2006/122077   11/2006

OTHER PUBLICATIONS

Evans et al (Molecular and Cellular Biochemistry 98: 135-140, 1990).*

(Continued)

*Primary Examiner* — Christian Boesen
(74) *Attorney, Agent, or Firm* — Knobbe, Martens, Olson & Bear, LLP

(57) ABSTRACT

A method for high throughput discovery of proteins fluorescently labeled at a cysteine residue and that undergo a change in fluorescence ratio at 2 wavelengths upon binding an unbound analyte is described. Probes are disclosed which are labeled at a cysteine residue and also probes labeled at both cysteine and lysine with two different fluorophores. These probes are useful for characterization and measurement of hydrophobic species in a fluid sample, particularly characterization and measurement of levels of unbound free fatty acids. A profile of unbound free fatty acids can be determined for an individual which can be used to determine the individual's relative risk for disease.

27 Claims, 13 Drawing Sheets

Figure 2B: HPLC trace of the V26C K27A I-FABP mutant. The 280 nm and the 375 nm traces correspond to protein and acrylodan respectively.

(56) References Cited

U.S. PATENT DOCUMENTS

2005/0244864 A1    11/2005  Kleinfeld et al.
2008/0261255 A1*   10/2008  Tolosa et al. .................. 435/15

OTHER PUBLICATIONS

Chattopadhyay, et al. "Measurement of Microsecond Dynamic Motion in the Intestinal Fatty Acid Binding Protein by Using Fluorescence Correlation Spectroscopy," *Proceedings of the National Academy of Sciences of the United States of America*, vol. 99, No. 22, pp. 14171-14176, Oct. 29, 2002.

Donato, et al. "A Fluorescence-based Method for Analyzing Retinoic Acid in Biological Samples," *Analytical Biochemistry*, vol. 357, No. 2, pp. 249-256, Oct. 15, 2006.

Supplementary European Search Report issued Dec. 20, 2010 to European patent application No. 09 70 1867.

International Search Report dated Mar. 30, 2009, issued to international application No. PCT/US2009/031341.

Kapanidis et al., "Fluorescent probes and bioconjugation chemistries for single-molecule fluorescence analysis of biomolecules," *Journal of Chemical Physics*, vol. 117(24), pp. 10953-10964 (Dec. 22, 2002).

Hibbs et al., "Acrylodan-conjugated Cysteine Side Chains Reveal Conformational State and Ligand Site Locations of the Acetylcholine-binding Protein," The Journal of Biological Chemistry, vol. 279(27), pp. 28483-28491 (Jul. 2, 2004).

* cited by examiner

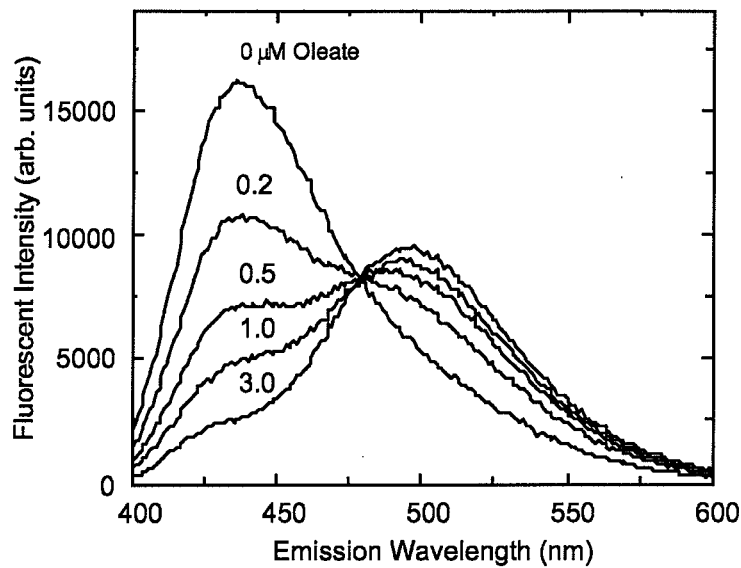
Figure 1A: Fluorescence emission spectra for ADIFAB during titration with sodium oleate at 22°C. Ex = 386 nm
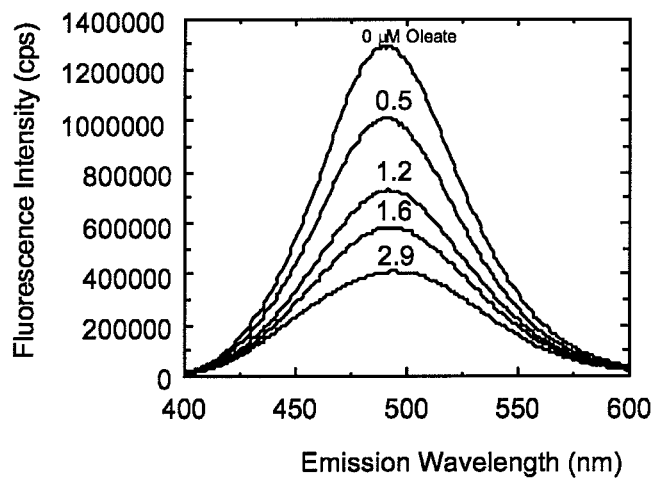
Figure 1B: Fluorescence emission spectra for ADIFAB K27C during titration with sodium oleate at 22°C. Ex = 386 nm.

Figure 1C: Fluorescence emission spectra for ADIFAB V26C K27A during titration with sodium oleate at 22°C. Ex = 386 nm.

Figure 2A: HPLC trace of ADIFAB. The 280 nm and 375 nm traces correspond to the protein and acrylodan respectively Figure 2B: HPLC trace of the V26C K27A I-FABP mutant. The 280 nm and the 375 nm traces correspond to protein and acrylodan respectively.

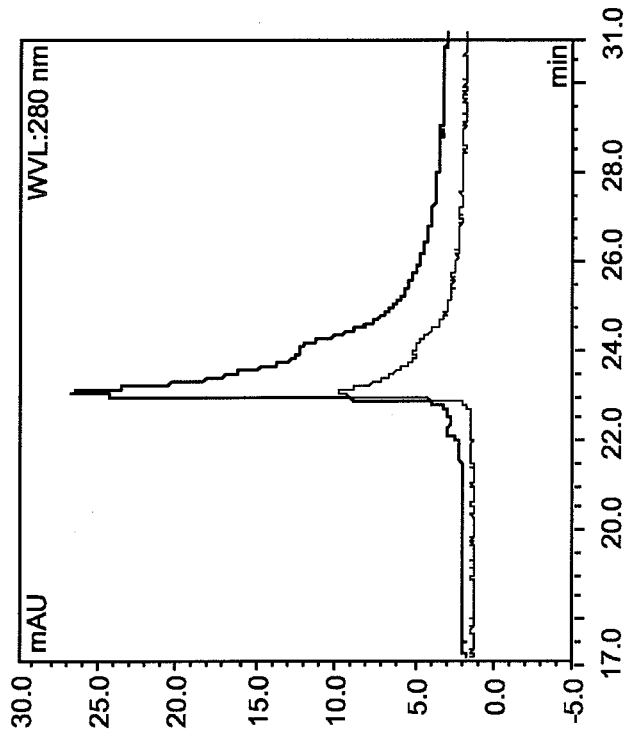
Figure 3B: L2P22G6 K27C
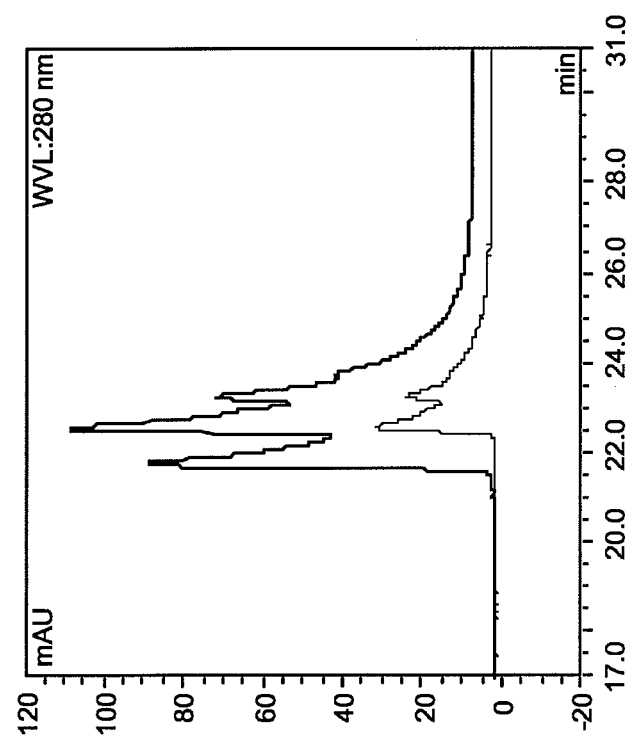
Figure 3A: L2P22G6.

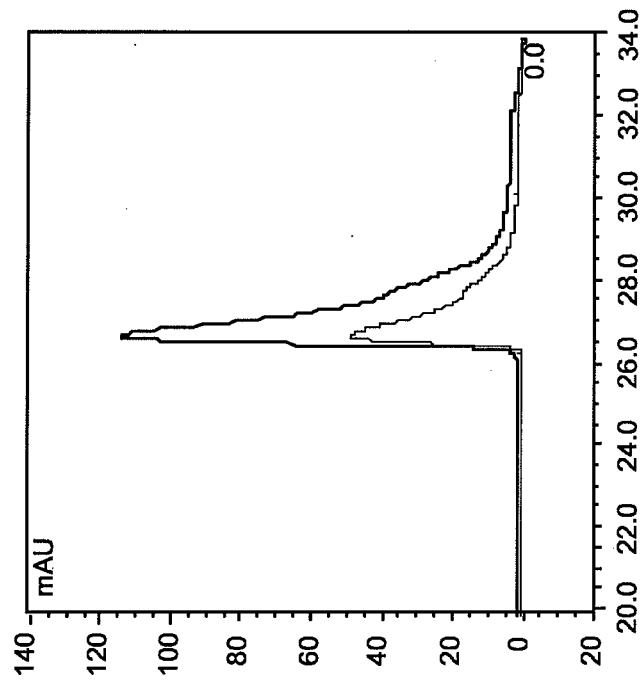
Figure 3F: L18P5G12 K27C
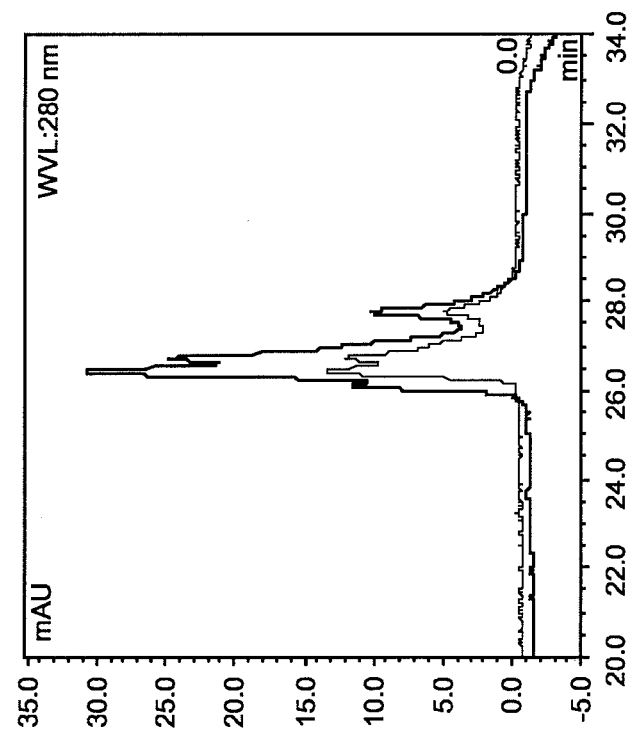
Figure 3E: L18P5G12

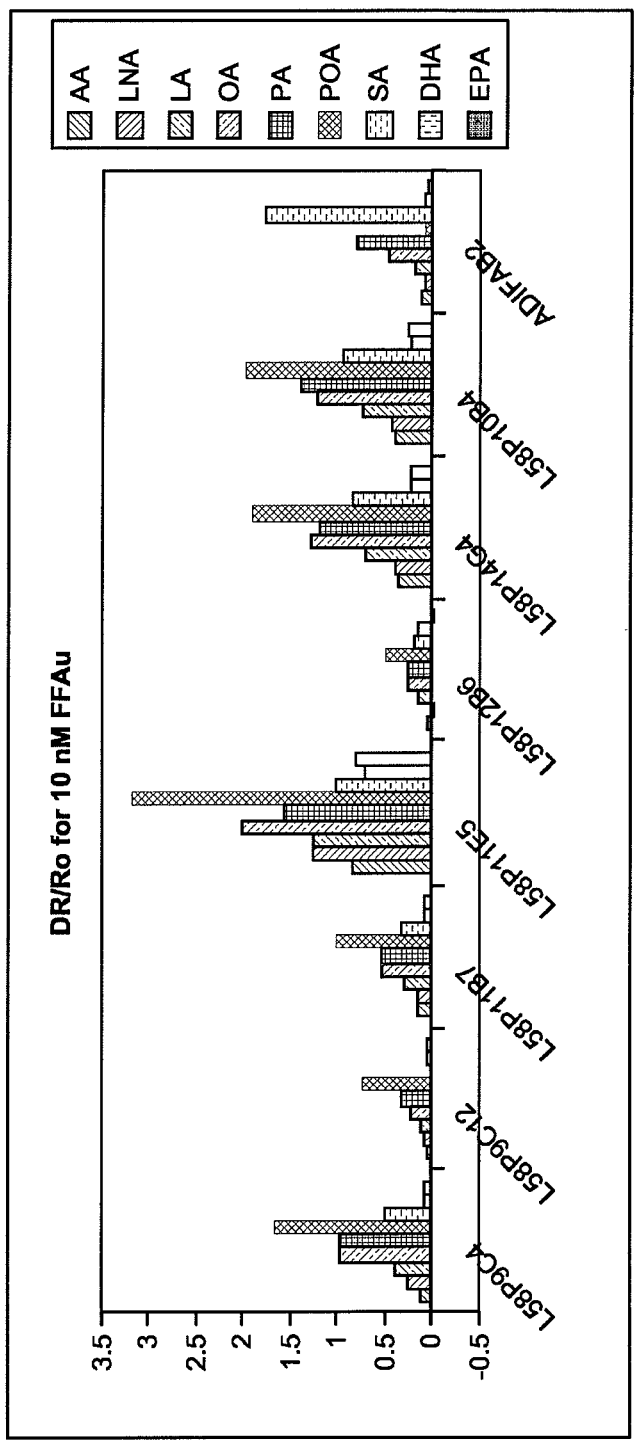
Figure 5a: probe response profiles from an L30C K27A library.

Figure 5b: probes response profiles from a V26C K27A library.

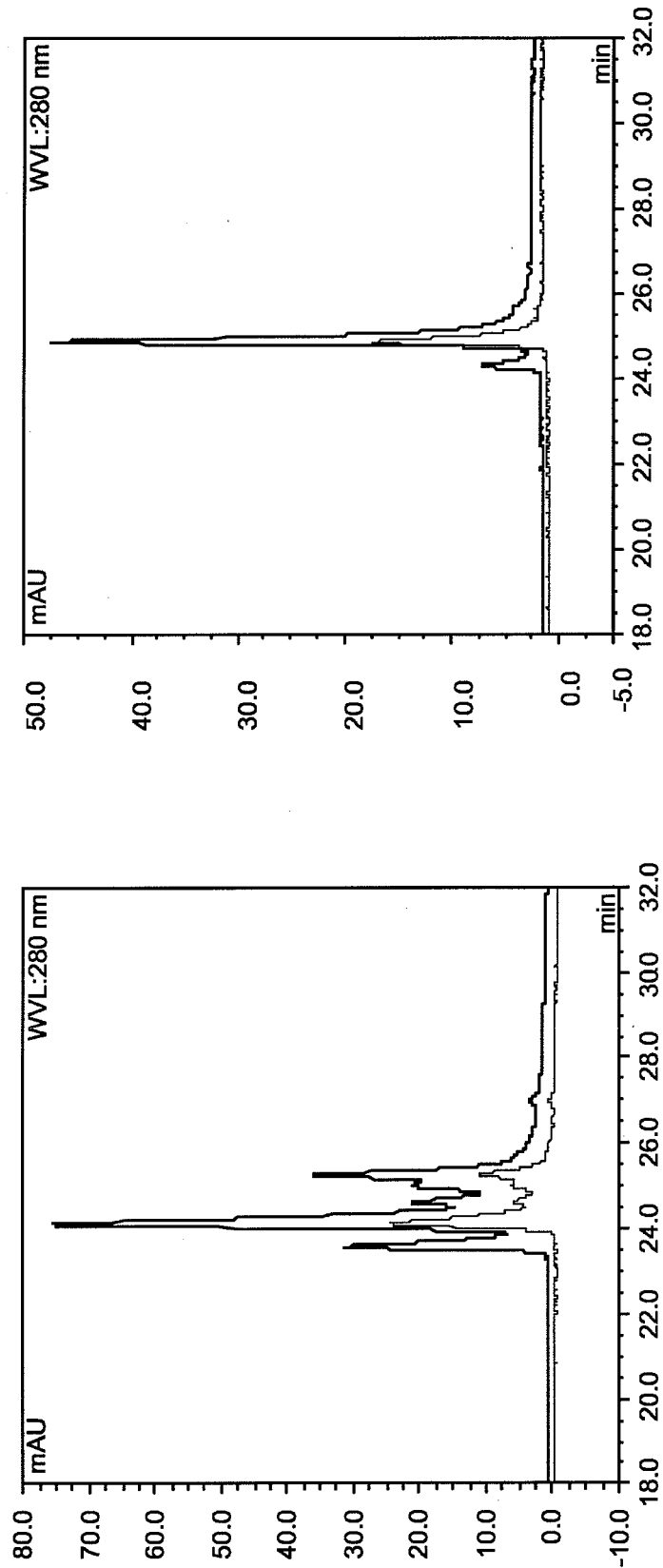
Figure 6D: L4BP17A3 - KR14
Figure 6C: L4BP17A3

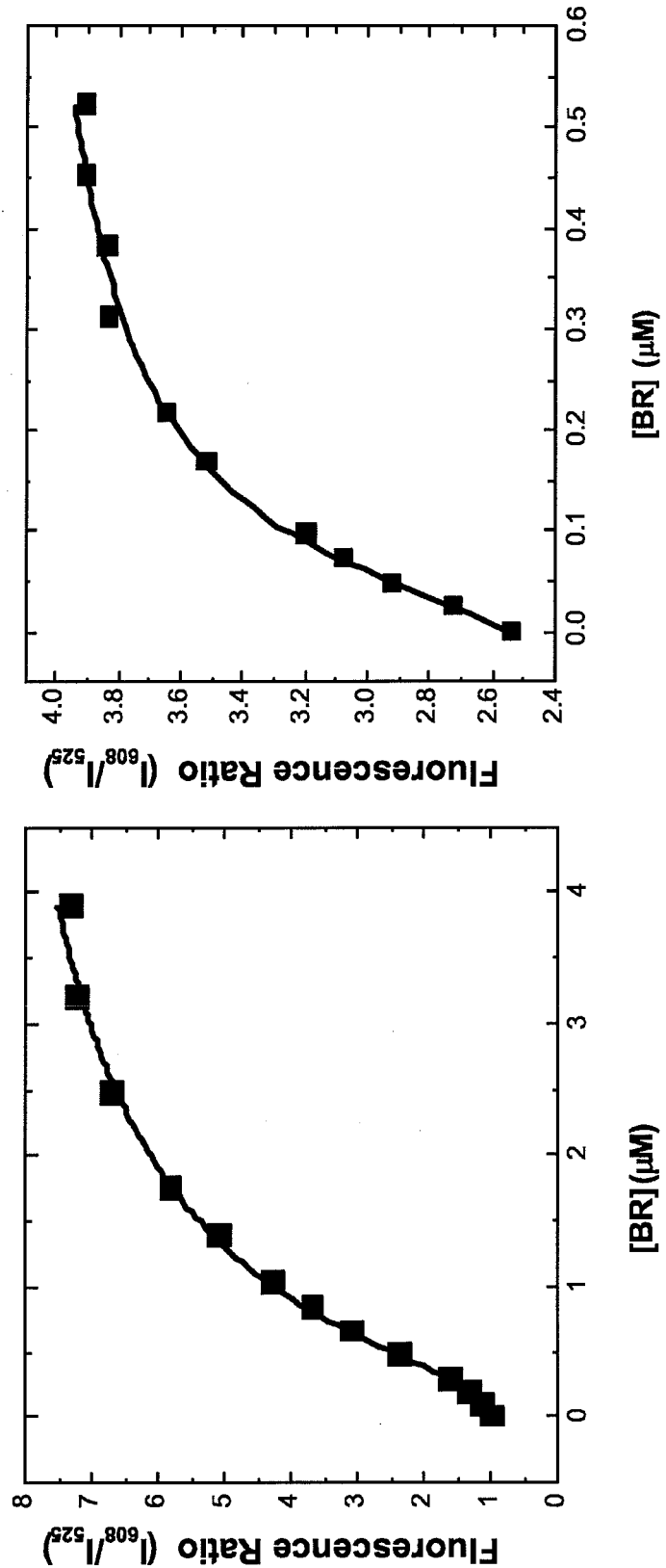
Figure 7A: Ratio response of double labeled (acrylodan and Texas Red) L2P14F7 with N-terminal MGCFD linker to increasing concentrations of bilirubin.
Figure 7B: Ratio response of double labeled (acrylodan and Texas Red) L2P14F7 KR14 with N-terminal MGCFD linker to increasing concentrations of bilirubin.

DEVELOPMENT AND USE OF CYSTEINE-LABELED FLUORESCENT PROBES OF UNBOUND ANALYTES

RELATED APPLICATIONS

This application claims priority to provisional U.S. Application No. 61/022,261, filed Jan. 18, 2008, which is incorporated herein by reference

STATEMENT REGARDING FEDERALLY SPONSORED R&D

This work was supported in part by Roadmap Grant No. R33 DK070314 and SBIR Grant No. R43 DK073535 from the National Institute of Health. Consequently, the U.S. government may have certain rights to this invention.

REFERENCE TO SEQUENCE LISTING

A sequence listing is included at the end of the specification.

BACKGROUND OF THE INVENTION

1. Field of the Invention

The field of the invention relates to high throughput discovery of proteins fluorescently labeled at a cysteine residue (probe) that undergo a change in fluorescence ratio at 2 wavelengths upon binding an unbound analyte and which probes are used to measure levels of unbound analytes, including unbound free fatty acids and other unbound metabolites.

2. Description of the Related Art

For purposes of the present disclosure, "analytes" are molecules whose molecular weight is approximately 2000 Da or less and unbound analytes are these molecules in aqueous solution. These include metabolites and physiologically important molecules that occur naturally in the course of human or animal physiology or pathophysiology, and drug molecules and their metabolic products and nutrient molecules and their metabolic products. Depending upon their solubility, a fraction of each analyte is present as monomers in aqueous solution (either charged or neutral). This fraction is referred to as the "unbound analyte" fraction and includes unbound metabolites (METu).

For purposes of the present disclosure, "fatty acids", a particular type of metabolite, are non-esterified carboxylated alkyl chains of 1-30 carbons atoms which may exist as neutral (e.g. protonated, sodium or potassium salt) or ionic species, depending upon the pH and conditions of the aqueous media. "Free fatty acids (FFA)" are equivalent to fatty acids and both terms refer to the totality of FFA including those in aqueous solution as monomers plus those that are not in solution (for example bound to other macromolecules (proteins, membranes), cells or part of an aggregate of FFA (micelles, soaps and other more complex aggregates). FFA present as monomers in aqueous solution (either charged or neutral) are referred to as "unbound free fatty acids (FFAu)".

For the purposes of the present disclosure, the term "lipid" is taken to have its usual and customary meaning and defines a chemical compound which is most soluble in an organic solvent but has some level of solubility in the aqueous phase (the fraction that is unbound). Accordingly, a "lipid-binding protein" includes any protein capable of binding a lipid as lipid is defined herein.

Levels of unbound molecules, such as for example lipids, hormones and metabolic products, can provide information diagnostic of health and disease when measured in appropriate human or animal fluids. It is increasingly apparent that determination of the unbound (a.k.a 'aqueous phase' or 'free') concentration of such molecules provides critical information about physiologic homeostasis. Many metabolites are hydrophobic molecules with low aqueous solubility and unbound concentrations that are much lower than their "total" concentration, where the bulk of the "total" may be bound to proteins or cells. In biological fluids the concentration of the unbound molecules is often regulated to maintain a relatively constant unbound concentration under normal physiologic conditions. This regulation occurs through the interaction of the molecules with a carrier protein such as for example, albumin. Thus most of the molecules are generally bound to albumin, or other carriers. However a small fraction of the molecules may dissociate (and rebind) from the albumin into the aqueous phase and these are the unbound molecules.

Intracellular lipid binding proteins (iLBP) are a family of low-molecular weight single chain polypeptides. There are four recognized subfamilies. Subfamily I contains proteins specific for vitamin A derivatives such as retinoic acid and retinol. Subfamily II contains proteins with specificities for bile acids, eiconsanoids, and heme. Subfamily III contains intestinal type fatty acid binding proteins (FABPs) and Subfamily IV contains all other types of fatty acid binding protein (Haunerland, et al. (2004) Progress in Lipid Research vol. 43: 328-349). The entire family is characterized by a common 3-dimensional fold. Ligand binding properties of the different subfamilies overlap considerably. The wild type proteins of subfamily I (Richieri et al (2000) Biochemistry 39:7197-7204) and subfamily II both bind fatty acids as well as their native ligands. Moreover, single amino acid substitutions are able to interconvert the ligand binding properties of proteins of subfamilies I and II (Jakoby et al (1993) Biochemistry 32:872-878).

U.S. Pat. No. 5,470,714 and U.S. Pat. No. 6,444,432, which are incorporated herein by reference, describe probes for the determination of unbound free fatty acids (FFAu). These probes were constructed using either native or mutant forms of proteins from the iLBP family. As discussed above, this family includes FABPs (Banaszak et al (1994) Adv. Protein Chem. 45:89-151; Bernlohr et al (1997) Ann. Rev. Nutrition, 17: 277-303). FABPs are intracellular proteins of approximately 15 kDa molecular weight and have a binding site that binds 1 or 2 FFA.

For the purposes of the present disclosure "probes" are iLBPs that are fluorescently labeled at a cysteine residue and that undergo a change in the ratio of a fluorescence index measured at different 2 wavelengths upon binding an analyte. A probe may also be an iLBP fluorescently labeled at a cysteine residue with one fluorophore and at a different, preferably lysine, residue with a different fluorophore so that if the fluorescence of only one of the fluorophores change upon binding an analyte the ratio of fluorescence indices at 2 wavelengths will be different. Such probes may be used to determine the aqueous concentration of specific unbound analytes including FFAu, METu and other lipophilic hormones, and drugs, which is otherwise difficult because of their poor solubility properties in aqueous solutions. A change in the ratio of the fluorescence response is essential for the accurate determination of the intracellular as well as extracellular concentrations of unbound analytes.

Unfortunately, despite the availability of protein structures and co-complex structures with ligands of interest, existing state of the art of molecular theory is not sufficient to design probes with any desired specificity and sensitivity de novo.

Thus, extensive experimentation is typically required to find protein probes that not only bind with the desired specificity, but also produce the required change in signal ratio indicative of ligand binding. Improving specificity and signaling through a completely random mutational strategy is not practical even for a small protein such as an FABP because a) there are $20^{131}$ possible mutants for a 131 residue FABP, and b) screening even a single probe for its binding specificity to a range of METu and other ligand molecules requires extensive time for purification, reaction chemistry and probe fluorescence response characterization.

Thus methods are needed to rapidly generate and screen thousands of resulting mutant probes. Each mutant needs to be produced, and chemically reacted with a fluorescent group, in sufficient quantity to enable the measurement of its sensitivity and selectivity for many different ligands (aka unbound analytes). It is also critical that the probes be as free as possible of contaminating proteins, unreacted fluorophore, and any other compounds that might interfere with sensitive fluorescence measurements. The development of a rapid, automated method for measuring and comparing probe responses to ligand is also critical.

Previously, probes found by these methods to be most effective in producing a change in signal ratio indicative of ligand binding were labeled with acrylodan primarily at the lysine 27 position of rat intestinal FABP of SEQ ID NO:2 or of mutations of SEQ ID NO:2 or SEQ ID NO 4 (Huber et al Biochemistry (2006) 45:14263-14274 and U.S. Pat. No. 7,601,510, which is incorporated herein by reference). Although labeling at the lysine position with environmentally sensitive fluorophores such as acrylodan results in probes that produce a fluorescence ratio change that is sensitive to ligand binding, we have found that the fluorophore labeling stoichiometry, the heterogeneity of labeling and the stability of the fluorophore-protein chemical bond, is mutant dependent. For example, acrylodan labeling of SEQ ID NO:2 or SEQ ID NO:2 with an L72A substitution, produce probes that are virtually completely labeled at a single lysine position (Lys 27) (for example, FIG. 2A. However, acrylodan labeling of other SEQ ID NO:2 muteins (SEQ ID NO:4) can result in probes that are not completely labeled and/or are labeled at more than a single position (for example FIG. 3).

Incompletely labeled muteins yield "probes" that are mixtures of fluorescently labeled and unlabeled muteins. As described previously (Richieri et al J. Biol. Chem. (1992) 267:23495-23501) the ligand (analyte) binding affinity is generally different for the labeled and unlabeled mutein and is usually smaller for the fluorescently labeled mutein than the unlabeled mutein. Moreover, typical variation in lysine labeling reaction conditions may result in lot-to-lot differences in the fraction of labeled and unlabeled mutein. This is an issue because the unbound ligand or analyte concentration determined using a probe that is a mixture of labeled and unlabeled mutein may be dependent upon the fraction of unlabeled mutein. This can occur because a significant fraction of the carrier (for example albumin) bound ligands (analytes) bind to the unlabeled mutein fraction of the probe solution. This effect may be exacerbated in the event that only a small fraction of the mutein is fluorescently labeled and therefore larger amounts of probe are required to yield a sufficiently intense fluorescence signal. Targeting lysine residues for fluorescence labeling is also potentially problematic because most iLBPs possess several lysine residues as well as a free N terminal amino group that can be labeled. In the event that multiple sites are labeled, the dynamic range of the probe's response to analyte binding will be compromised and the response may not reveal a single isoemissive point.

Mutating the iLBP protein to contain a single cysteine and using conditions to fluorescently label only cysteines should produce a homogenously labeled protein. However, substituting cysteine for lysine at position 27 of SEQ ID NO:2 followed by reaction with acrylodan results in fluorescently labeled protein that does not generate a fluorescence ratio change upon ligand binding (for example, FIG. 1B or IAN-BDE in Kleinfeld U.S. Pat. No. 5,470,714). Also in Kleinfeld '714 it is found that labeling the I-FABP mutants Thr81Cys or Thr83Cys with acrylodan yields a fluorescent protein that is unresponsive to FFAu binding. Other studies of fluorescently labeled cysteine iLBPs yield either a complete lack of sensitivity to ligand binding as in rat liver FABP (Evans and Wilton, Mol. Cell. Biochem. (2004) 98:135-140) or reveal a lack of change in ratio as in the CRABP proteins (Donato and Noy Anal Biochem (2006) 137:249-256). Thus methods are needed to generate cysteine labeled probes that exhibit the ratio response of the lysine labeled probes (Huber et al Biochemistry (2006) 45:14263-14274 and U.S. Pat. No. 7,601,510, which is incorporated herein by reference).

Embodiments of the invention described here satisfy these needs by disclosing methods for discovering locations for cysteine substitutions that allow rapid a) generation of large numbers (a library) of cysteine labeled mutein probes and the b) screening and of these probes to discover probes with different specificities for sets of unbound analytes and that respond to analyte binding by a change in fluorescence ratio. An important aspect of this invention is that it allows the previous necessary and very time consuming step of characterization of ligand binding to the protein to be omitted; only the probe itself is characterized. This is important not only for the avoidance of the protein characterization step but also because the properties of the probe are often not predictable from the ligand-protein binding characteristics. For example, different proteins can have very similar binding affinities but the fluorescence response of their derivative probes can be quite different.

Additional embodiments of the invention described here are methods for reducing the potential for fluorescence labeling at multiple lysine sites by mutating sets of lysines to arginine, thereby leaving only one fluorophore reactive site. Also described are methods to generate probes that are labeled with 2 different fluorophores. Such probes respond to analyte binding with a change in the ratio of a fluorescence index measured at two different wavelengths. This allows probes that do not reveal a ratio fluorescence index change in response to analyte binding to be converted into a ratio probe by labeling with a second fluorophore that reveals no or significantly reduced response to the binding of the analyte.

SUMMARY OF THE INVENTION

Embodiments of the invention are directed to a high throughput method for generating and screening of probes which includes one or more of the following steps:
 (a) generating polynucleotides encoding a protein library having an assortment of iLBP muteins with a cysteine residue from a polynucleotide template to generate a library of iLBP muteins;
 (b) expressing the iLBP muteins;
 (c) purifying the iLBP muteins by binding to a solid matrix;
 (d) associating the matrix-bound iLBP muteins with a single fluorophore or two different fluorophores to produce probes;
 (e) retrieving the probes from the solid matrix;
 (f) screening each probe in a fluorometer in the presence and absence of a set of unbound analytes of interest each with defined unbound concentrations to determine binding of each probe to the set of unbound analytes of interest;

(g) observing a change in the ratio of a fluorescence index measured at two different wavelengths of the probes in the presence and absence of the unbound analytes; and (h) characterizing each of the probes according to a set of fluorescence responses of each of the probes to the set of analytes of interest. Preferably, the fluorescence index is intensity, polarization and/or lifetime of the probe, in the presence and absence of each analyte in the set of analytes of interest. In preferred embodiments, the fluorophore is covalently attached to the cysteine residue.

In preferred embodiments, the unbound analyte is an unbound metabolite. More preferably, the unbound metabolite is an unbound free fatty acid.

In preferred embodiments, the iLBP encoded by the template is a Fatty Acid Binding Protein (FABP), or variant thereof that retains the capability of binding an analyte.

Preferably, the polynucleotide template encodes iLBP muteins having a cleavable or noncleavable affinity tag. More preferably, the template polynucleotide template encodes iLBP muteins having a poly-histidine affinity tag and the solid matrix includes an immobilized metal chelate.

In preferred embodiments, the iLBP muteins are labeled with a single fluorophore at a pH of less than 8 so that the fluorophore preferentially reacts with the cysteine sidechain. Preferably, the fluorophore is acrylodan, danzyl aziridine, 4-[N-[(2-iodoacetoxy)ethyl]-N-methylamino]-7-nitrobenz-2-oxa-1,3-diazole ester (IANBDE), or 4-[N-[(2-iodoacetoxy)ethyl]-N-methylamino]-7-nitrobenz-2-oxa-1,3-diazole (IANBDA).

In alternate preferred embodiments, the iLBP muteins are labeled with a first fluorophore and a second fluorophore. Preferably, the one fluorophore is acrylodan, danzyl aziridine, 4-[N-[(2-iodoacetoxy)ethyl]-N-methylamino]-7-nitrobenz-2-oxa-1,3-diazole ester (IANBDE), or 4-[N-[(2-iodoacetoxy)ethyl]-N-methylamino-7-nitrobenz-2-oxa-1,3-diazole (IANBDA). Preferably, the other fluorophore is a longer wavelength absorbing and emitting fluorophore such as Alexa Fluor dyes, Bodipy, fluorescein derivatives, rhodamine derivatives or Texas Red. In some preferred embodiments, labeling includes reacting cysteine with the first fluorophore at pH less than or equal to 8; and reacting lysine with the second fluorophore at pH greater than 8. In other preferred embodiments, labeling includes reacting cysteine with the first fluorophore at pH less than or equal to 8; and reacting the amino terminus of the iLBP mutein with the second fluorophore.

In some embodiments of the invention, a second fluorophore is provided by addition of an acceptor protein or peptide domain to each of the iLBP muteins. Preferably, the acceptor protein or peptide domain is selected from the group consisting of a bi-functional polypeptide fused to a protein that can be cross-linked to a solid phase (SNAP-Tag®, CLIP-Tag® and ACP-Tag™) and the like. In some embodiments, the polynucleotide mutants in the library contain a nucleotide segment encoding a fluorescent protein. Preferably, the acceptor protein domain or the fluorescent protein has zero or a significantly reduced response in intensity and/or wavelength of emitted fluorescence upon binding to the analytes in the set of unbound analytes of interest compared to the fluorescence of the iLBP mutein portion of the probe.

In preferred embodiments, the analytes are complexed with a carrier macromolecule such as albumin, lipid binding proteins, lipid vesicles or cyclodextrin. The complex of the analytes and the carrier macromolecule buffers the concentration of the unbound analyte which provides clamping of a level of unbound analyte. In preferred embodiments, the carrier macromolecule is albumin.

In some embodiments, steps (d) and (e) are replaced with one or more of the following steps:
washing the bound iLBP muteins;
removing the iLBP muteins from the solid matrix; and
reacting the unbound iLBP muteins with a single fluorophore or two different fluorophores to produce probes.

In preferred embodiments, the method also includes mutating the iLBP muteins having a cysteine residue to replace all surface accessible lysine residues with any other amino acid, preferably arginine or alanine before associating the iLBP muteins with the fluorophore.

In alternate preferred embodiments, the method includes mutating the iLBP muteins having a cysteine residue to replace all but one surface accessible lysine residues with any other amino acid, preferably arginine or alanine before associating the iLBP muteins with the fluorophore. In preferred embodiments, the iLBP mutein template (SEQ ID NO: 5) has 15 surface accessible lysines. Muteins with the KR14 designation have the lysines at positions 7, 16, 20, 29, 37, 46, 50, 88, 92, 94, 100, 125, 129 and 130 mutated to arginine.

Preferred embodiments are directed to identifying probes with desirable characteristics by determining a value for R by the following formula:

$$R = F\lambda 1 / F\lambda 2$$

$F\lambda 1$ is a measured fluorescence intensity (intensity of a probe with analyte present minus intensity of the analyte without the probe present) at a first emission wavelength, $F\lambda 2$ is a measured fluorescence intensity (intensity of a probe with analyte present minus intensity of the analyte without the probe present) at a second emission wavelength. The difference between R in the presence and absence of the analyte is measured by the formula $$\Delta R = R_{+analyte} - R_0$$

$R_{+analyte}$ is the ratio value for the measurement done in the presence of the analyte and $R_0$ is the ratio value for the measurement done in the absence of the analyte. $\Delta R$ for the probe is compared to $\Delta R_{reference}$ for a standard.

In some preferred embodiments, the standard is the fluorescent probe made from the protein encoded by the polynucleotide template used to generate mutations for the high throughput screening. In some preferred embodiments, the standard is acrylodan labeled rat intestinal fatty acid binding protein (ADIFAB) or acrylodan labeled Leu72 to Ala mutant of the rat intestinal fatty acid binding protein (ADIFAB2).

In some preferred embodiments, $\Delta R$ for the probe is and $\Delta R_{reference}$ for the standard are positive, that is $R_{+analyte} > R_0$ for probe and reference. In some preferred embodiments, $\Delta R$ for the probe is negative, that is $R_{+analyte} < R_0$ for the probe.

In preferred embodiments, probes are screened with n unbound analytes and a probe is found for which *$\Delta R$*/$\Delta R$reference, where *$\Delta R$* is the absolute value of $\Delta R$, is largest and >0.1 for one or more of the n unbound molecules and is at least 0.1 smaller for the remaining unbound molecules. Preferably, the unbound analytes are unbound metabolites. More preferably, the unbound metabolites are unbound fatty acids.

Embodiments of the invention are directed to an iLBP mutein having a single cysteine labeled with a fluorescent dye. Preferably, any surface lysines with fluor labeling activity under cysteine-specific labeling conditions are replaced with another amino acid, preferably alanine. In the preferred embodiment, which utilizes an iLBP mutein template corresponding to SEQ ID NO: 5, the lysine at position 27 is highly reactive and is mutated, typically to alanine.

In some preferred embodiments, the iLBP mutein has a single cysteine and a single lysine each labeled with a fluorescent dye.

Preferably, the fluorescent dye is acrylodan. Preferably, the iLBP is a fatty acid binding protein.

In preferred embodiments, the iLBP mutein corresponds to SEQ ID NO: 5 having at least one mutation at a position selected from 8, 11, 14, 17, 18, 21, 23, 24, 26, 27, 30, 31, 34, 36, 38, 40, 47, 49, 51, 53, 55, 56, 58, 60, 62, 68, 70, 71. 72, 73, 74, 75, 76, 78, 80, 82, 89, 91, 93, 95, 102, 104, 106, 113, 115, 117, 119, and 126 or to a homolog thereof having at least one mutation at a position homologous to a position selected from 8, 11, 14, 17, 18, 21, 23, 24, 26, 27, 30, 31, 34, 36, 38, 40, 47, 49, 51, 53, 55, 56, 58, 60, 62, 68, 70, 71. 72, 73, 74, 75, 76, 78, 80, 82, 89, 91, 93, 95, 102, 104, 106, 113, 115, 117, 119, and 126 of SEQ ID NO: 5.

In preferred embodiments, the iLBP mutein corresponds to SEQ ID NO: 5 having cysteine inserted at a position selected from 21, 23, 24, 25, 26, 27, 28, 29, 30, 31, 55, 74, 73, and 76 of SEQ ID NO: 5 or at a position homologous to a position selected from 21, 23, 24, 25, 26, 27, 28, 29, 30, 31, 55, 74, 73, and 76 of SEQ ID NO: 5.

In preferred embodiments, all surface accessible lysine residues are substituted with an amino acid residue that is not lysine, preferably arginine or alanine. In other preferred embodiments, all but one surface accessible lysine residue is substituted with an amino acid that is not lysine, preferably arginine or alanine.

Preferred embodiments of the invention are directed to an iLBP mutein which is L10P7A4-L30C, L11P7B3-V26C, L13EP16E11, L18P5G12-K27C, L50BP4E2, L50BP9D5, L61P8B12, L68P3H10, or L71AP22B3. Other preferred embodiments are directed to iLPP muteins which are bilirubin specific probes such as L2P14F7-MGCFD-TR and L2P14F7-KR14-MGCFD-TR.

Embodiments of the invention are directed to fusion proteins having an iLBP with a single cysteine labeled with a fluorescent dye fused with a fluorescent protein.

Embodiments of the invention are directed to protein chimeras having an iLBP with a single cysteine labeled with a fluorescent dye and an acceptor protein or peptide domain. Preferably, the acceptor protein or peptide domain is a SNAP-tag, CLIP-tag, ACP-tag or a biotinylation tag. These tags are then labeled with a second fluorophore of interest.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

FIG. 5 shows probe responses given as $\Delta R/R_o$ for the 9 FFAu listed in the box (arachidonate (AA), linolenate (LNA), linoleate (LA), oleate (OA), palmitate (PA), palmitoleate (POA), stearate (SA), docosahexanoate (DHA), and eicosapentaenoate_(EPA), each at 10 nM. The ADIFAB2 response is included for reference. The L58 library is POA and the L69 library is DHA specific. FIG. 5A shows probe response profiles from a L30C K27A library.

FIG. 7 shows Bilirubin binding isotherms for two dual fluorophore bilirubin ratio probes synthesized by labeling with acrylodan and Texas red. FIG. 7A shows the ratio response to increasing concentrations of bilirubin of double labeled (acrylodan and Texas Red) L2P14F7 with the N-terminal Ala substituted with GC. FIG. 7B shows the ratio response to increasing concentrations of bilirubin of double labeled (acrylodan and Texas Red) L2P14F7 KR14 with N-terminal MGCFD linker.

DETAILED DESCRIPTION OF THE PREFERRED EMBODIMENT

Figure 1C:
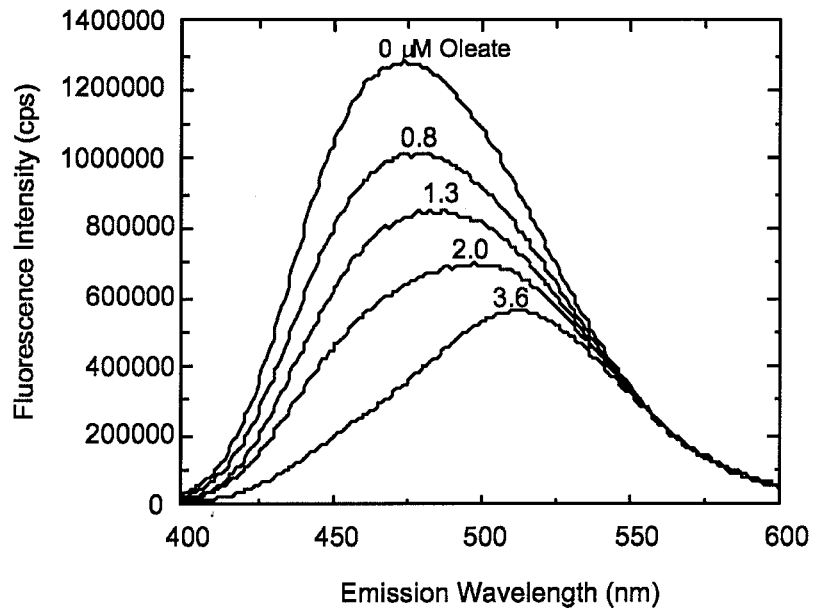
FIG. 1 Fluorescence spectra for ADIFAB (FIG. 1A), the K27C (FIG. 1B) and the V26C K27A (FIG. 1C) SEQ 2 mutants having terminal arg-gly at positions 132-133 and a his6× tag with increasing oleic acid at 22° C. Ex=386 nm.

While the described embodiment represents the preferred embodiment of the present invention, it is to be understood that those skilled in the art can modify the process without departing from the spirit of the invention.

Preferred embodiments of the present invention relate to the development of fluorescent protein molecules that can be used to determine the concentration of unbound analytes. More particularly, the invention relates to 1) high throughput methods to discover such probes, 2) the use of such probes for clinical medicine, drug development and basic science, 3) examples of the development of probes for the determination of the unbound concentration of specific free fatty acids, 4) the use of such probes to provide a profile of unbound metabolites for monitoring the states of health and disease for early diagnosis of human disease and for monitoring the effect of therapeutic intervention on the course of a condition or disease. Other uses include drug screening and monitoring the effect of a nutrient. It is noteworthy that for each probe described, there is cross reactivity between the various categories of metabolites. For example, a probe may bind strongly to retinoic acid but, still have some binding affinity for fatty acids. The probes according to embodiments of the invention find utility in identification and quantification of a wide range of metabolites.

Probes are proteins that have been 'labeled' through the covalent addition of one or more fluorescent molecule(s) (fluorophore(s)) that exhibit a change in the ratio of fluorescent indices measured at 2 different wavelengths. In preferred embodiments, the probe contains a single cysteine to which a fluorophore is covalently attached. In other preferred embodiments, the probe includes one fluorophore attached to a cysteine and a second fluorophore attached to a different site, preferably a lysine site, on the protein which binds metabolites. In other preferred embodiments the probe includes one fluorophore attached to a cysteine and a second fluorophore attached to a different site, preferably a terminal amino group, on the protein which binds metabolites. Probes have the characteristic that their fluorescence undergoes a change in the ratio of fluorescence indices in a measurable way when they bind metabolites.

In some embodiments, two different fluorophores are used, preferably attached to a cysteine and a lysine or to a cysteine and an N-terminus amino group. One of the two fluorophores is environmentally sensitive, that is, demonstrating a change in a fluorescence index upon binding of an analyte. The second fluorophore may be environmentally sensitive but it is not necessary for the second fluorophore to be environmentally sensitive. The second fluorophore provides a reference point so that a difference in ratio of fluorescence at two different wavelengths is observed upon analyte binding. The second fluorophore may not react to the ligand binding or may react in a different manner from the first fluorophore. Preferably, the second fluorophore has an emission point at a longer wavelength relative to the first fluorophore. Examples of chemical dyes which may be used as a second fluorophore according to the invention include but are not limited to Alexa Fluor dyes, Bodipy dyes, fluorescein derivatives, rhodamine derivatives and Texas red. In a preferred embodiment, the second fluorophore is Texas red dye.

Reacting the side chain of the amino acid to which the fluorophore is to be attached is performed under conditions favorable for the side chain or N-terminus which is the target attachment site. For example, when labeling cysteine, the reaction is carried out at pH less than or equal to 8, preferably 4-8, more preferably around 5.8 to 7.2. When labeling lysine, the reaction is carried out at alkaline pH, greater than 8, preferably 8.8 to 9.5.

Different probes can be generated by mutating the starting (template) protein and labeling the mutated proteins (muteins) with a fluorophore (s). In preferred embodiments, the starting proteins are mutated to include cysteine residues, preferably a single cysteine residue for attachment of a fluorophore. In some preferred embodiments, the starting protein is mutated further to either delete surface accessible lysine residues or replace one or more surface accessible lysine residues with another amino acid residue, preferably arginine or alanine, thereby reducing potential for introducing fluorophores at more than one site. Surface accessible sites can be determined from structural information that is known and available for iLBP's. In other preferred embodiments, at least one surface accessible lysine is retained for attachment of a second fluorophore to the lysine side chain. The ability of each such probe to respond to a particular metabolite (or analyte) can then be assessed by measuring the change in fluorescence upon addition of defined concentrations of the unbound metabolite.

Generating the Library

A library of proteins representing potential probes may be created by any means known in the art. In a preferred embodiment, a protein that is capable of binding one or more unbound metabolites may be used as a template for mutagenesis. In the preferred embodiments, the protein capable of binding one or more unbound metabolites is from the iLBP family for proteins including retinol/retinoic acid binding proteins, bile salt binding proteins, and Fatty Acid Binding Proteins (FABP). The protein may bind fatty acids, other metabolites or both fatty acids and other metabolites. Besides free fatty acids, possible metabolites include but are not limited to molecules such as drugs, drug metabolites, hormones, prostaglandins, leukotrienes, sphingosine, sphingolipids, phospholipids, glycolipids, cholesterol and cholesterol derivatives and other steroids, lipid-soluble vitamins, bile salts, enzyme cofactors, retinoids such as retinoic acid and retinal, heme and heme metabolites, amino acids, peptides, carbohydrates and multivalent ions.

In more preferred embodiments, a FABP gene, wild-type or mutant, is used as the initial template or starting point for mutagenesis. A collection of mutant FABP clones is generated from the template. In preferred embodiments, mutation involves one or more amino acid substitutions in the binding cavity or the helical cap of the FABP. In a preferred embodiment, a mutant Rat Intestinal Fatty Acid Binding Protein (rI-FABP), which has 131 amino acid residues, was used as the starting point for the mutagenesis.

In more preferred embodiments, sites that alter ligand binding are predominantly ones that are within the binding cavity or on the alpha helices that form the protein "cap" of the FABP. Sites that do not alter ligand binding are predominantly ones that are on the surface of the protein. In some embodiments, a library may be constructed by choosing among the sites that alter ligand binding and then applying random mutagenesis to those sites. Some single site mutants in the stated "cavity" or "cap" may not produce soluble protein or may fail to significantly affect binding. However, the same mutant, when combined with other mutations, may cause significant and favorable changes in ligand binding specificity. Such sites can also be selected experimentally as candidates for multi-site mutagenesis or library construction Any number of mutagenesis methods may be used to generate a collection or "library" of mutants. Mutagenesis methods include but are not limited to error-prone PCR, site-directed mutagenesis using defined or degenerate oligonucleotides, splicing by overlap extension (SOE), gene shuffling, or the use of mutator host strains. In preferred embodiments, an oligo-directed method of PCR-based mutagenesis was used to generate a collection or "library" of mutants. However, as far as the screening is concerned, it doesn't matter whether the library is composed of known, specific site-directed mutants or an "unknown" random assortment of mutants. Both types of libraries are screened with the same efficiency.

In preferred embodiments, oligos specifying desired mutations prime an enzymatic copying of the vector containing the template gene. The oligo, and therefore the desired mutation(s), is incorporated into the new copy of the gene. The sites mutated in the multi-site mutagenesis libraries of the preferred embodiments are those that were found to alter ligand-binding properties in a library of single point mutants.

Mutant genes are introduced into an organism capable of producing soluble protein from the mutant gene. Any type of organism can be used as long as soluble protein can be harvested from the lysed cells or the cell growth medium. For example, bacteria are used for protein expression in the preferred embodiment, but one skilled in the art could also express the protein in yeast, insect or other eukaryotic cells.

Producing the Probes

Protein purification is accomplished by incubating lysate from each clone with a solid support to which the protein is specifically bound with high affinity. There are two ways to make the protein associate with a solid support: a) the protein can be changed to increase its affinity for a solid support or b) the support can be modified to increase its affinity for the protein. The latter can be accomplished, for example, by immobilizing antibodies on the solid support, said antibodies having a high binding-affinity for the protein of interest.

Alternatively the protein may be "tagged" so that it binds to the solid support with high affinity. This includes but is not limited to tagging with biotin, Flag-epitope or c-myc epitope or HA-tag, glutathione-S-transferase (GST), maltose binding protein (MBP), a chitin binding domain (CBD), Thioredoxin, β-Galactosidase, VSV-Glycoprotein, calmodulin binding protein, or a metal affinity tag such as a 6×His tag. Preferably, the fusion partner does not change the FABP fatty acid binding properties. The specific association of the affinity tag with the solid support material enables single step purification of the protein of interest from the lysate, which contains thousands of other contaminating proteins and other substances. The affinity tag(s) may be fused at either the $NH_2$— or COOH— termini or at both termini simultaneously. In a preferred embodiment, a 6× Histidine tag was fused to either the FABP $NH_2$— or COOH— termini or at both termini simultaneously without significantly changing the protein's fatty acid binding properties. These fusion proteins can be reversibly immobilized on a solid support for protein purification, delipidation and probe production.

In the process described here, the muteins are affinity purified and left on the affinity purification matrix, essentially making the protein part of the solid phase. Chemical functionalities required for delipidation, labeling, and removal of unreacted label are passed over the protein/solid phase. Since the probe is assayed directly, rather than assay of an unlabeled protein indirectly, the signal is much stronger and very small quantities of probe are required (<8 µg).

By this method a large number of muteins may be constructed, purified, fluorescently labeled and the probes screened for ligand binding in a high throughput format. In a preferred embodiment, the cell growth, cell lysis, protein purification, fluorescent labeling, and probe purification is done in multiwell plates. Preferably, the plates have from 1 to 1536 wells and each well has a volume of between 0.002 ml to 10 ml. By this method, probes may be generated which have different fluorescent responses to different fatty acids or other metabolites as compared to the response of the template. For example, the probe variants may each have different fluorescence spectra and/or different fluorescence intensity at a given emission wavelength when bound to a particular fatty acid as compared to the parent template.

In preferred embodiments, the protein variants are labeled at a cysteine residue with acrylodan while still bound to the solid support. Any other fluorophore which undergoes a change in fluorescent index in response to a change in environment may be used instead of acrylodan. Such fluorophores include but are not limited to danzyl aziridine, 4-[N-[(2-iodoacetoxy)ethyl]-N-methylamino]-7-nitrobenz-2-oxa-1,3-diazole ester (IANBDE), and 4-[N-[(2-iodoacetoxy)ethyl]-N-methylamino-7-nitrobenz-2-oxa-1,3-diazole (IANBDA). If a second fluorophore is used, the second fluorophore is reacted with the protein variants after labeling the first fluorophore. If the first fluorophore is environmentally sensitive then the second fluorophore should be relatively inert to environmental changes and should have a fluorescence emission measurably different than the first fluorophore.

In some preferred embodiments, one fluorophore is reacted with the mutant iLBP domain and the second fluorophore is provided by either fusing a fluorescent protein (FP) to the iLBP domain or by the specific labeling of a 'target' or 'acceptor' protein domain or peptide that has been fused to the mutant iLBP domain. It is now common practice to produce fluorescently tagged proteins inside cells by creating a gene for the production of a fusion protein (a.k.a. protein chimera) between the protein of interest and a fluorescent protein such as Green or Red Fluorescent Protein (GFP or RFP). Fluorescent proteins do not require a chemically synthesized label. Any person with normal skill in the art could, with minimal experimentation, fuse an iLBP to one of the many available fluorescent proteins or their mutants. Preferentially, one of the published fluorescent muteins with a red-shifted spectrum would serve as the second label in probe construction. Any surface cysteines on the FP not involved in disulfide formation would be mutated to a different amino acid.

Protein chimeras generated with an iLBP mutein and an acceptor protein domain or peptide would also work well. As in the case of the iLBP-FP fusion, the labeled acceptor portion of the chimera provides a fluorescent signal that reveals no or significantly reduced response to the binding of the analyte, but does allow for the creation of a fluorescence ratio probe. A significantly reduced response to the binding of the analyte means that the response is a change in fluorescence intensity that is more than 0 but less than one/tenth of the response produced by the binding to the iLBP mutein portion of the protein chimera, preferably less than one twentieth and more preferably less than one/one hundredth of the response observed by binding of the analyte to the iLBP mutein portion of the protein chimera.

There are several tagging technologies for the sequence-specific addition of a fluorophore to an acceptor protein or peptide domain. Three systems, the SNAP-tag, the CLIP-tag, and the ACP-tag, are sold by New England Biolabs (Ipswich, Mass.). The SNAP-tag is a 20 kDa mutant of the DNA repair protein $O^6$-alkylguanine-DNA alkyltransferase. The SNAP-tag reacts specifically and rapidly with fluorescent derivatives of benzylguanine. The CLIP-tag also utilizes a mutant of $O^6$-alkylguanine-DNA alkyltransferase. The CLIP-tag reacts specifically with fluorescent derivatives of $O^2$-benzylcytosine. The ACP-tag utilizes a phosphopantetheinyl transferase, typically from B. subtilis or E. coli, to covalently attach 4'-phosphopantetheinyl groups from Coenzyme A (CoASH) to a specific serine residue. The acceptor peptide sequence containing the serine can be as small as 12 residues and the enzyme accommodates a large number of different groups attached to the free thiol of CoASH. Thus, it is straightforward to generate fluorescent CoASH derivatives by reacting CoASH with cysteine-reactive fluorophores and then using the phosphopantetheinyl transferase to transfer the fluorophore to protein chimera containing the acceptor peptide. A conceptually very similar enzymatic labeling scheme uses E. coli biotin ligase (BirA) to transfer a ketone isostere of biotin to a 15 amino acid acceptor peptide. The covalently coupled ketone is then specifically conjugated to hydrazide- or hydroxylamine-functionalized fluorophores.

In a preferred embodiment, the template FABP is recombinant rat intestinal fatty acid binding protein (rI-FABP) mutein with a cysteine mutation. Labeling the protein with acrylodan is performed using known methods substantially as previously described (U.S. Pat. No. 5,470,714 & Richieri, G. V, et al., J. Biol. Chem., (1992) 276: 23495-23501). The wavelength emitted by the fluorescently-labeled FABP depends upon the label and protein used. The wavelengths at the maximum intensities emitted by these acrylodan-labeled I-FABP's in the absence of FFA is about 420 to 480 nm. The emission wavelengths at the maximum intensities emitted by these acrylodan-labeled I-FABP's with FFA bound is about 495 to 580 nm. Experiments typically involve measuring the fluorescence response within both emission maxima or at wavelengths for which the effect of interfering molecules such as hemoglobin can be eliminated as described in U.S. application Ser. No. 10/670,958 and PCT/US2004/030521, which are incorporated herein by reference, and the calculation of the ratio 'R' of the two fluorescence intensities. The baseline value for this ratio, measured in the absence of analyte, is designated Ro.

Probes produced according to some embodiments of the invention have altered specificity for different FFAu or different unbound metabolites relative to the ADIFAB and ADIFAB2 probes made from the preferred templates. Altered specificity refers to an alteration in the fluorescence change that occurs when the probe is exposed to different unbound metabolites or different molecular species of FFAu (for example different chain lengths and/or different numbers of double bond and/or different rotational isomers about a given double bond and/or different locations of double bonds.) For example, ADIFAB2 might reveal, when exposed to a particular FFAu1 at a concentration of [FFAu1], a change ($\Delta R1$) in the value of the ratio R relative to Ro. Exposing ADIFAB2 to n different such FFAu would reveal a set of responses, $\{\Delta Ri\}=\Delta R1i, \Delta R2i, \ldots \Delta Rni$. This set of responses $\{\Delta Ri\}$ is defined as the "response profile for probe i" also termed "probe i response profile". A different probe with altered specificities would possess a different set of responses to the same set of n FFAu and concentrations; $\{\Delta Rj\}=\Delta R1j, \Delta R2j, \ldots \Delta Rnj$. Therefore $\{\Delta Rj\}$ is the response profile for probe j. With sufficient numbers of different probes possessing different responses it would be possible by measuring the response of each probe to a sample containing mixtures of different FFAu and/or different unbound metabolites, to determine the concentration of each different FFAu and/or different unbound metabolite. Because different states of health and disease might alter the distribution of different FFAu and/or different unbound metabolites in a variety of body fluids including but not limited to whole blood, blood plasma, blood serum, urine, CSF, saliva, gastric juices, interstitial fluid, synovial fluid or lymph, it can be expected that such a determination would provide valuable information about health status. In addition, such measurements would provide valuable tools for basic research and drug discovery.

Screening the Probes

In some embodiments, aliquots of the probes prepared as described above are placed in multi-well plates, suitable for fluorescence measurements. Defined amounts of unbound analytes are added to each well and a fluorescence signal from the wells containing probe and analytes are compared to wells containing only the probe. The values obtained are compared with those of a 'reference' probe. The analytes may be fatty acids or other unbound metabolites. Preferably, the number of wells in the multiwell plate is between 1 and 1536. Preferably, the fluorescence signal is measured from each well with a fluorescence plate reader to determine if the signals of each probe are significantly different than those of the parent probe. For many analytes it is important that they be added to each well in complex with a carrier molecule, for example albumin, to buffer the unbound analyte and thereby clamp its concentration to well defined values. Clamping ensures that the concentration of analyte in the aqueous phase in the well is unaffected by binding to the surfaces of the well or the probes themselves. Clamping is essential for discovery of probes because analytes have different solubilities and therefore different affinities for surfaces. Highly insoluble analytes added without proper clamping may bind to the surfaces and be unavailable for binding to the probe. In this example the probe might incorrectly give the appearance of no response to the insoluble analyte. Thus to determine the correct response profile (specificities) for each probe each analyte's concentration must be clamped.

The fluorescence intensity ratio ("R" value) for a given probe is determined. The ratio is calculated using the following formula:

$$R=F_{\lambda 1}/F_{\lambda 2}$$

wherein, $F_{\lambda 1}$ is the measured fluorescence intensities (intensity of the probe with the analyte present minus intensity of the analyte without probe present) at wavelength 1 and $F_{\lambda 2}$ is the measured fluorescence intensities (intensity of the probe with the analyte present minus intensity of the analyte without probe present) at wavelength 2. Then, for a given probe, $\Delta R$, the difference in R value between the measurement in the presence of each analyte and in the absence of each analyte, is calculated as follows:

$$\Delta R = R_{+analyte} - R_0$$

The $\Delta R$ value for a given probe is then compared to a reference probe, for example, ADIFAB or ADIFAB2, by $\Delta R/\Delta R_{reference}$. This value is an indication of how dissimilar the new probe (derived by mutation of the template) is to the reference. By this method, probes with new and useful characteristics may be identified. Measurements of fluorescence intensities are obtained using standard techniques.

Preferably, the fluorescence intensities at two or more wavelengths are measured in each well and the intensity ratios at all combinations of the two or more wavelengths are evaluated to determine if the ratios of each probe for a set of analytes are significantly different than those of the reference probe. By this method, probes may be identified that have different specificities in their fluorescence response to different analytes as compared to the reference probe. In preferred embodiments, the analytes are unbound free fatty acids. Other methods for comparing changes in fluorescence with and without analytes can also be used.

Using the Probes

A collection of probes with distinct signaling properties can be used to determine the concentrations of different unbound metabolites in a mixture, for example the concentrations of different unbound free fatty acids in a mixture. Thus, an unbound metabolite and/or an unbound free fatty acid profile can be determined for an individual. Such determinations are used to generate, for any individual, a profile of unbound FFA that is useful in the diagnosis of disease and the determination of risk factors for disease.

DNA and protein sequences for Fatty Acid Binding Proteins (FABPs) are shown in the sequence listing. SEQ ID NO: 1 shows the cDNA sequence for the wild-type rat intestinal Fatty Acid Binding Protein (rIFABP). The rat fatty acid binding protein is post-translationally modified in the rat, with the modifications including the removal of the N-terminal methionine and the acetylation of the "new" N-terminal residue Ala. Protein sequences are numbered starting with the first residue of the mature protein. Thus, Ala is residue 1 in the corresponding protein shown as SEQ ID NO: 2.

SEQ ID NO: 3 shows a preferred template rI-FABP-L72A cDNA sequence according to the invention. SEQ ID NO: 4 shows the corresponding protein sequence. In this preferred embodiment, the protein has a substitution of alanine at position 72. Preferred species which are derived from the protein shown as SEQ ID NO: 5 are the probes listed in Table 1.

Preferred embodiments of the invention include a protein based upon the rat intestinal FABP of SEQ ID NO: 5 with one mutation in which a cysteine is substituted for the amino acid residue at one of the positions 21, 23, 24, 25, 26, 27, 28, 29, 30, 31, 55, 74, 73, or 76 and with zero or more mutations at positions 8, 11, 14, 17, 18, 21, 23, 24, 26, 27, 30, 31, 34, 36, 38, 40, 47, 49, 51, 53, 55, 56, 58, 60, 62, 68, 70, 71. 72, 73, 74, 75, 76, 78, 80, 82, 89, 91, 93, 95, 102, 104, 106, 113, 115, 117, 119, or 126. Preferably, the mutations are substitutions, insertions or deletions.

Preferred embodiments of the invention include a functional engineered protein based upon the rat intestinal FABP of SEQ ID NO: 5 with a fluorescence label at a cysteine sidechain at one of the residue positions 21, 23, 24, 25, 26, 27, 28, 29, 30, 31, 55, 74, 73, or 76 that is fluorescently labeled and with zero or more mutations at positions 8, 11, 14, 17, 18, 21, 23, 24, 26, 27, 30, 31, 34, 36, 38, 40, 47, 49, 51, 53, 55, 56, 58, 60, 62, 68, 70, 71. 72, 73, 74, 75, 76, 78, 80, 82, 89, 91, 93, 95, 102, 104, 106, 113, 115, 117, 119, or 126 and that have a value of $\Delta R/\Delta R_{ADIFAB2}$ with an unbound analyte which is more than 0.1. Preferably, the mutations are substitutions, insertions or deletions.

Certain embodiments of the invention pertain to a polynucleotide that includes a nucleotide sequence encoding a functional engineered protein that is:

(a) a protein including an amino acid sequence of rat intestinal FABP with a cysteine substituted for one of the residue positions 21, 23, 24, 25, 26, 27, 28, 29, 30, 31, 55, 74, 73, or 76 shown in SEQ ID NO:5 and zero or more mutations at a position 8, 11, 14, 17, 18, 21, 23, 24, 26, 27, 30, 31, 34, 36, 38, 40, 47, 49, 51, 53, 55, 56, 58, 60, 62, 68, 70, 71. 72, 73, 74, 75, 76, 78, 80, 82, 89, 91, 93, 95, 102, 104, 106, 113, 115, 117, 119, or 126, or (b) a protein that can be fluorescently labeled at a cysteine substituted for one of the residue positions 21, 23, 24, 25, 26, 27, 28, 29, 30, 31, 55, 74, 73, or 76 of SEQ ID NO: 5 and zero or more additional mutations which has a value of $\Delta R/\Delta R_{ADIFAB2}$ with an unbound analyte which is more than 0.1. Also encompassed are expression vectors including a polynucleotide according to the invention operably linked to at least one expression control sequence, and recombinant host cells that include the expression vector. The recombinant host cell may be a prokaryotic or eukaryotic cell.

Certain embodiments of the invention pertain to a polynucleotide that includes a nucleotide sequence encoding a functional engineered protein that is:

(a) a protein including an amino acid sequence of one of the family of lipid binding proteins that include but are not limited to fatty acid binding, bile acid binding and retinoid binding proteins, having three dimensional structures similar to rat intestinal FABP and with a cysteine substituted at one of the sites homologous to rat intestinal FABP SEQ ID NO: 2's sites 21, 23, 24, 25, 26, 27, 28, 29, 30, 31, 55, 74, 73, or 76 and zero or more additional mutations at sites homologous to rat intestinal FABP SEQ ID NO: 2 at a positions 8, 11, 14, 17, 18, 21, 23, 24, 26, 27, 30, 31, 34, 36, 38, 40, 47, 49, 51, 53, 55, 56, 58, 60, 62, 68, 70, 71. 72, 73, 74, 75, 76, 78, 80, 82, 89, 91, 93, 95, 102, 104, 106, 113, 115, 117, 119, or 126; or (b) a lipid binding protein that can be fluorescently labeled at a cysteine substituted at one of the sites homologous to rat intestinal FABP SEQ ID NO: 2's sites 21, 23, 24, 25, 26, 27, 28, 29, 30, 31, 55, 74, 73, or 76 and zero or more mutations at sites homologous to rat intestinal FABP SEQ ID NO: 2' at positions 11, 14, 17, 18, 21, 23, 31, 34, 36, 38, 40, 47, 49, 51, 53, 55, 60, 62, 68, 70, 72, 73, 74, 78, 80, 82, 89, 91, 93, 102, 104, 106, 113, 115, 117, 119, and 126 sites of rat intestinal FABP SEQ ID NO: 2 and which has a value of $\Delta R/\Delta R_{ADIFAB2}$ with an unbound metabolite which is more than 0.1. One skilled in the art could readily determine homologous sites based upon structural information that is known and available for LBP's. Also encompassed are expression vectors including a polynucleotide according to the invention operably linked to at least one expression control sequence, and recombinant host cells that include the expression vector. The recombinant host cell may be a prokaryotic or eukaryotic cell.

In preferred embodiments of the invention, the sample used for the determination of unbound FFA is a fluid sample derived from a human, an animal or a plant. Preferably, the fluid is whole blood, blood plasma, blood serum, urine, CSF, saliva, gastric juices, interstitial fluid or lymph. In some embodiments, unbound metabolites such as unbound FFA are extracted from tissue samples by means known in the art. In other embodiments determination of unbound metabolites such as unbound FFA is performed within the cytoplasm of a cell by microinjecting or otherwise transfecting the probe into the cell. Unbound metabolites include but are not limited to unbound FFA, drugs, drug metabolites, hormones, prostaglandins, leukotrienes, sphingosine, sphingolipids, phospholipids, glycolipids, cholesterol and cholesterol derivatives and other steroids, lipid-soluble vitamins, bile salts, enzyme cofactors, retinoids such as retinoic acid and retinal, heme and heme metabolites, amino acids, peptides, carbohydrates and multivalent ions. Classes of unbound free fatty acids include saturated, unsaturated, monounsaturated, polyunsaturated, short chain, medium chain and long chain.

A normal range for a given unbound metabolite is determined from a healthy population and deviations from this normal range may indicate disease. For example, elevated levels of unbound FFA are indicative of cardiac disease. In some embodiments, a metabolic profile is determined for an individual using more than one probe to determine levels of more than one unbound metabolite. Metabolic profiles from a normal, healthy population will be determined Deviations from a normal metabolic profile are indicative of disease, nutrient deficiency, exposure to toxins or carcinogens and the like.

In some embodiments, probes produced as described above are used to determine the effect of a drug on a known metabolic profile. The metabolic profile is determined for a test population which may be a normal or non-normal population such as a diseased population. For example, a metabolic profile may be determined for a diseased test population. The diseased test population could then be treated with a drug for a predetermined period of time. The metabolic profile is then redetermined for the test population after drug treatment to observe the effect of the drug on the metabolic profile. In some cases, a change in the metabolic profile may be undesirable, for example, if testing a drug for toxicity and/or unwanted side effects. In other embodiments, a change in metabolic profile may indicate the effectiveness of the drug tested.

In some embodiments, a drug therapy in a diseased patient is monitored using one or more probes prepared according to the invention. For example, a body fluid may be withdrawn from the patient. Binding of an unbound metabolite indicative of a disease may be tested using at least one probe produced as described herein. An abnormal level of one or more unbound metabolites is an indicator of a disease state. For example, elevated free fatty acids are risk factors and indicators of cardiovascular disease; deficiencies in vitamins B6 and folic acid have also been associated with cardiovascular disease and cancer. Levels of the unbound form of these metabolites may be measured or monitored according to the invention using probes generated as described herein.

In some embodiments, the metabolic profile may be used to determine the effect of specific nutrients on an individual. A metabolic profile may be used to indicate a nutrient deficiency.

In some embodiments, a metabolic profile may be used to classify individuals into different categories having different susceptibilities to different drugs and/or nutrients. In preferred embodiments, principal component analysis may be used to cluster unbound metabolite profiles into defined groups.

Example 1

ADIFAB, which is the rat intestinal FABP (SEQ ID NO:2) labeled with acrylodan at lysine 27 reveals a red shift in its fluorescence emission spectrum upon binding FFA (FIG. 1a). This response which reveals an isoemissive point can be used to relate the ratio of the fluorescence intensities at two wavelengths, for example 505 nm and 432 nm, to the concentration of the unbound FFA (Richieri et al J. Biol. Chem. (1992) 267:23495-23501). This is an example of the type of fluorescence response that is a necessary characteristic of a probe. In contrast, mutating lysine 27 of SEQ ID NO:2 to cysteine and labeling the cysteine with acrylodan results in a fluorescent protein that, although it is responsive to FFA binding by revealing a quenching of fluorescence, does not reveal a change in emission wavelength upon FFA binding and can therefore not be considered a probe (FIG. 1B). However, if instead of mutating lysine 27 to cysteine, lysine 27 is mutated to alanine and, valine at position 26 is mutated to cysteine and this cysteine is labeled with acrylodan, the resulting fluorescent protein reveals a red shift in fluorescence upon binding FFA (FIG. 1c). This V26C K27A mutant of SEQ ID NO:2 yields a ratio response upon FFA binding and is therefore a probe. This example illustrates that altering specific sites can yield effective probes.

Acrylodan labeling of lysine residues was carried out at pH 9.3 (as described in U.S. Pat. No. 7,601,510 which is incorporated herein by reference) while labeling of the cysteine residues was carried out at pH 7.0. In brief, the protein variants are preferably labeled with acrylodan while still bound to a solid support as part of the protein purification process. However, in other embodiments, the purified and delipidated protein may be labeled using a buffer exchange process with a fluorophore reaction buffer followed by chromatography steps to remove unreacted fluorophore. Other fluorescent labels may also be used such as but not limited to danzyl aziridine, 4-[N-[(2-iodoacetoxy)ethyl]-N-methylamino]-7-nitrobenz-2-oxa-1,3-diazole ester (IANBDE), and 4-[N-[(2-iodoacetoxy)ethyl]-N-methylamino-7-nitrobenz-2-oxa-1,3-diazole (IANBDA). Derivatization with acrylodan is performed using known methods substantially as previously described (U.S. Pat. No. 5,470,714 & Richieri, G. V, et al., J. Biol. Chem., (1992) 276: 23495-23501).

Figure 2A:
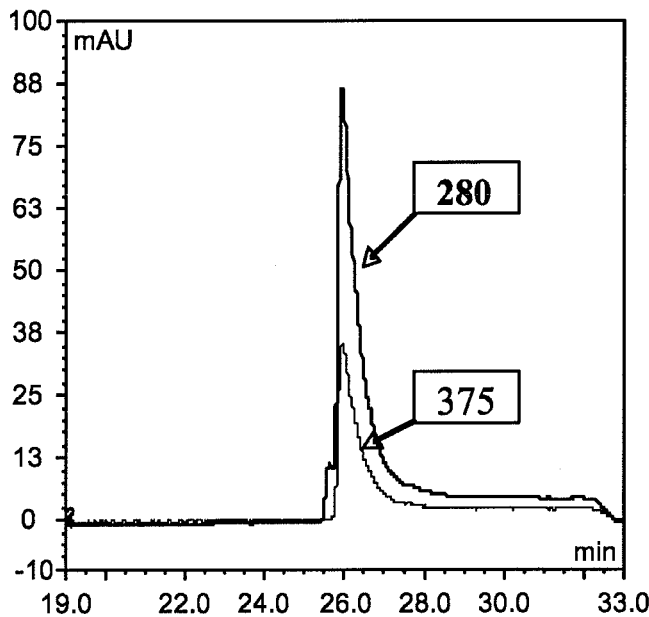
FIG. 2 HPLC chromatograms of ADIFAB (FIG. 2A) and the V26C K27A mutant (FIG. 2B). The 280 nm and 375 nm traces correspond to protein and acrylodan, respectively.
Figure 2B:
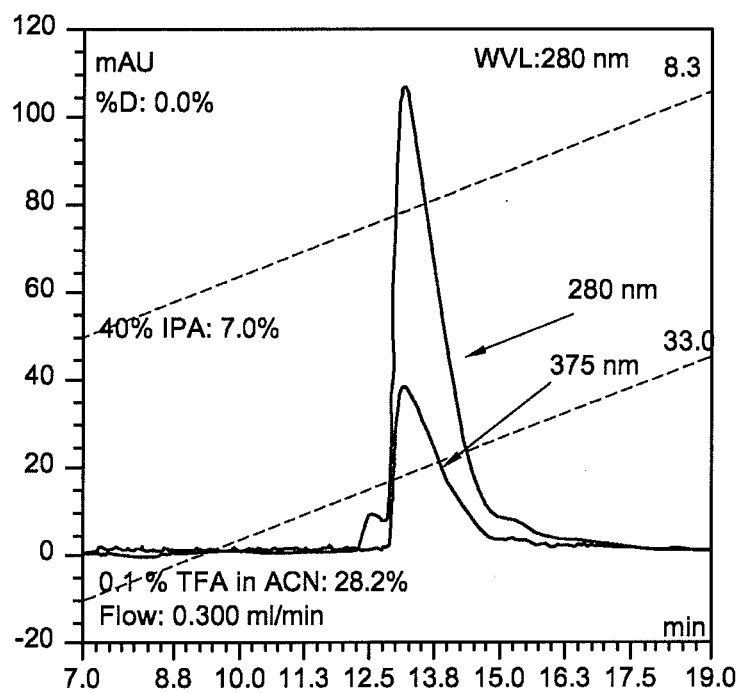

For ADIFAB, the K27C (not shown) and V26C K27A mutants of SEQ ID NO:5, the labeling was largely homogeneous as indicated by the HPLC results of FIG. 2.

Example 2

Figure 3D:
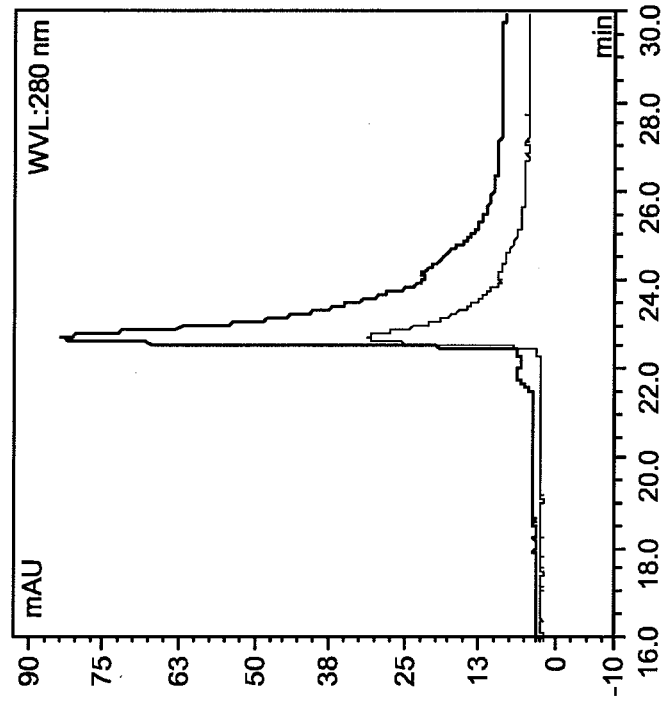
FIG. 3 shows examples of absorbance results for HPLC chromatograms of probes transformed from lysine (FIGS. 3A, 3C, 3E) to cysteine (FIGS. 3B, 3D, 3F) labeling with acrylodan. The upper trace is for the protein (280 nm) and the lower trace for acrylodan (375 nm).
Figure 3C:
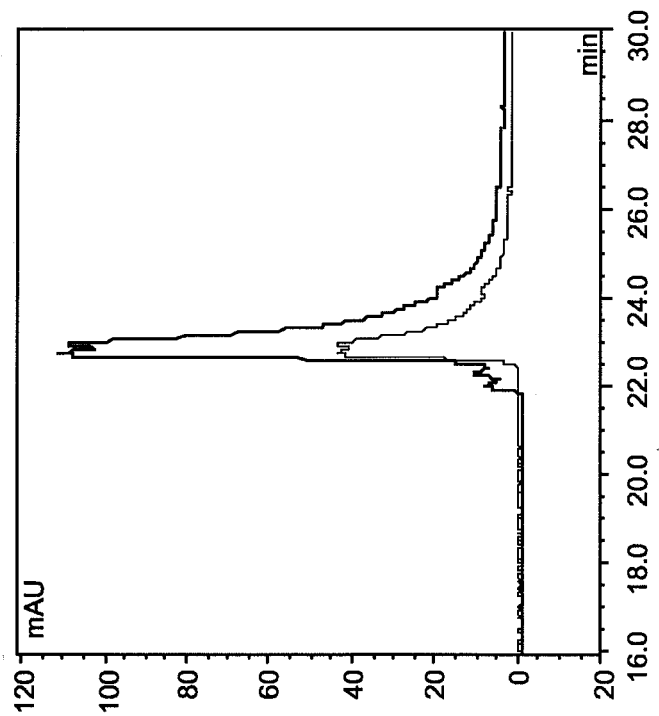
Figure 4B:
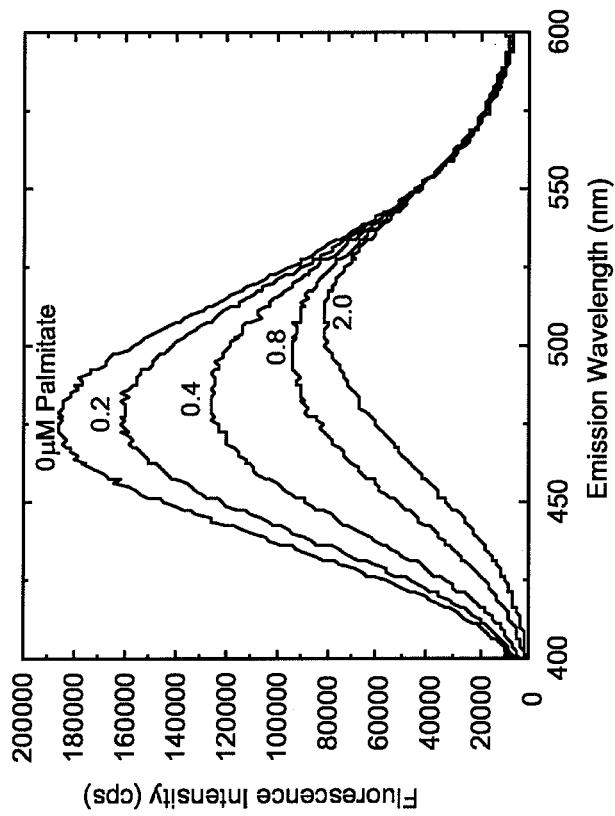
FIG. 4 shows fluorescence emission spectra for lysine (FIGS. 4A, 4C) and cysteine (FIGS. 4B, 4D) probes. The L2 probes are palmitate specific and sodium palmitate titration spectra are shown. The L11 probes are stearate specific and sodium stearate titration spectra are shown.
Figure 4A:
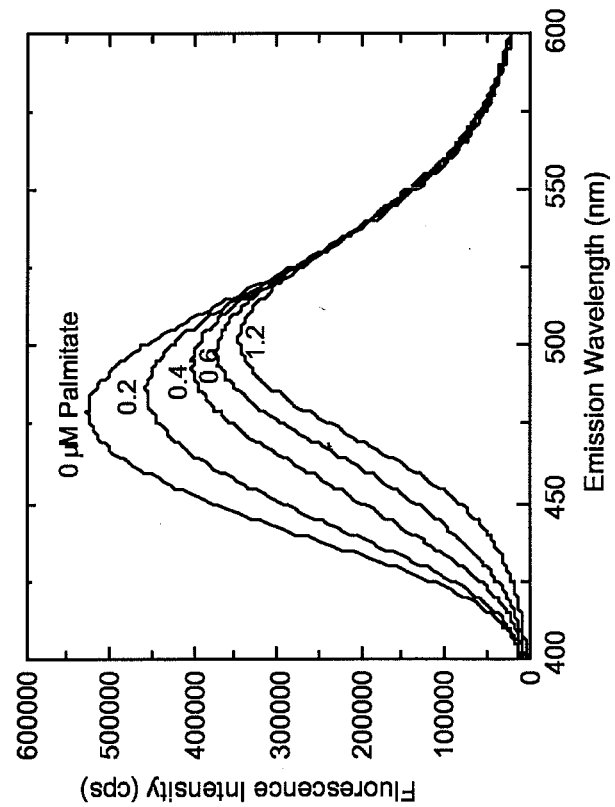
Figure 4D:
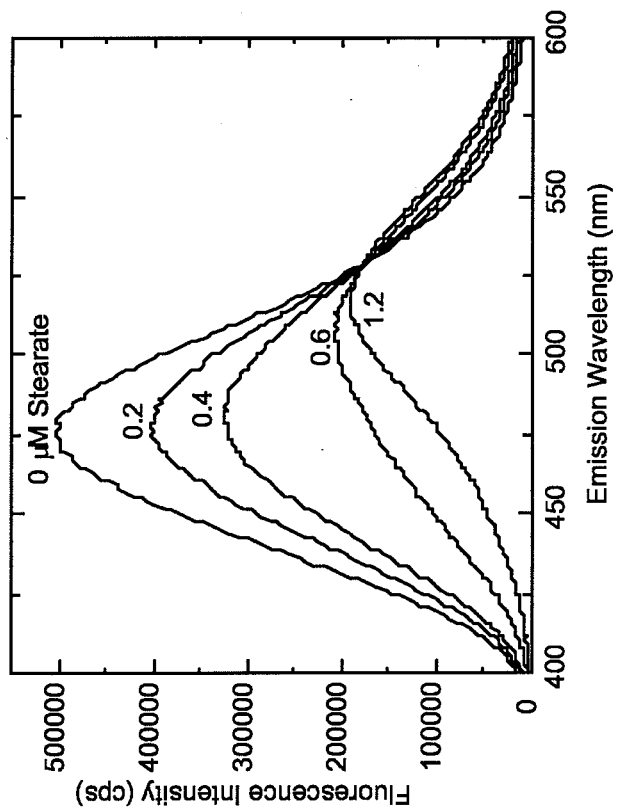
Figure 4C:
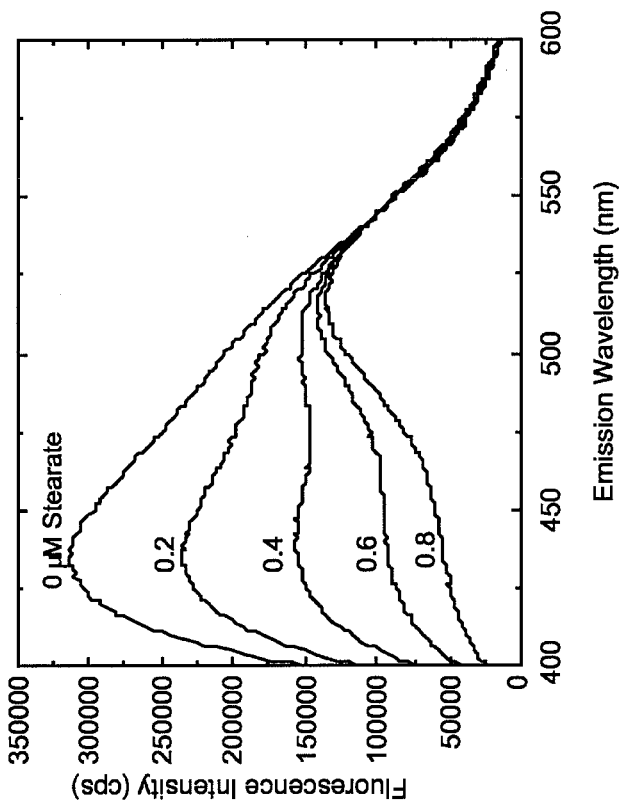

Several lysine labeled probes, revealing high sensitivity and specificity for particular FFAu, but exhibiting unfavorable labeling profiles because of a lack of labeling homogeneity and/or poor labeling stoichiometry were converted to cysteine labeled probes. This was done by substituting cysteine for the wild type side chains at several sites from the group M21, I23, N24, V25, V26, K27, R28, K29, L30, G31, F55, D74, A73 or T76 depending upon the probe mutations. The HPLC traces shown in FIG. 3 illustrates the labeling improvement for such 3 examples (Huber et al Biochemistry (2006) 45:14263-14274). Each of these cysteine substitutions resulted in responsive probes with very similar FFAu profiles as the lysine probes (FIG. 4).

Example 3

Figure 5B:
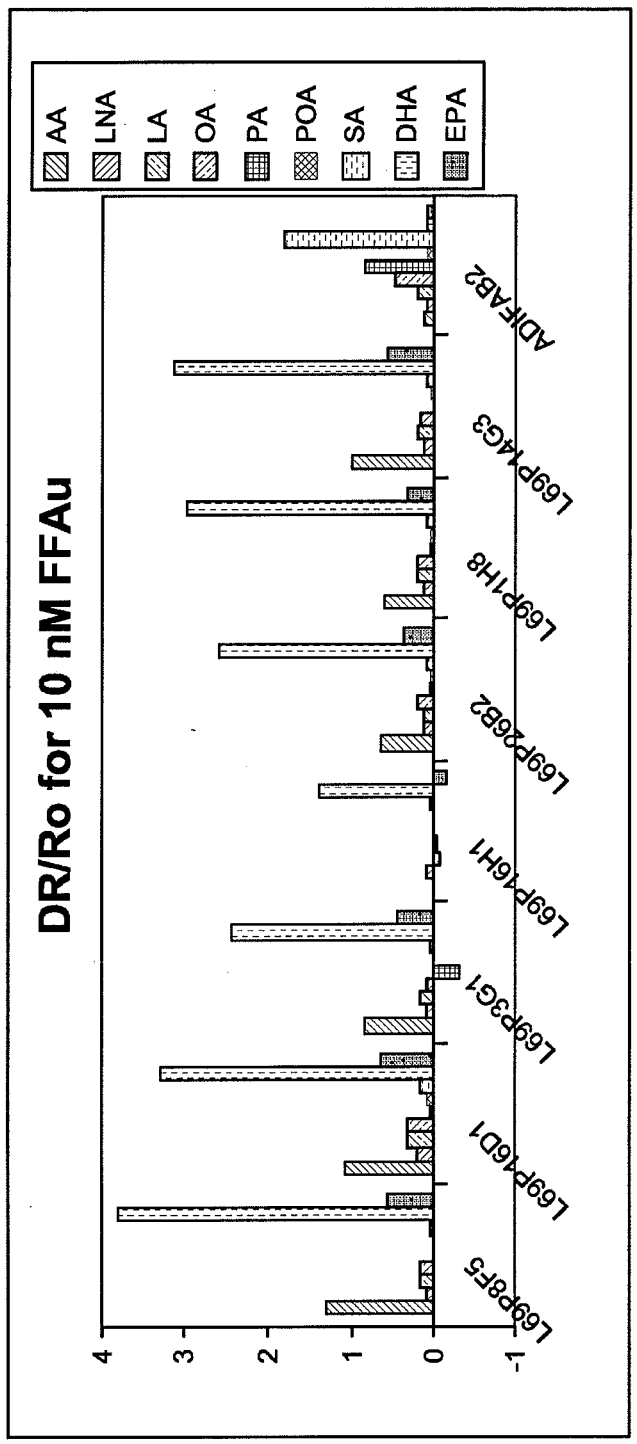
FIG. 5B shows probe response profiles from a V26C K27A library.

More than 40 libraries of cysteine-labeled mutant probes, using templates derived from SEQ ID NO: 5, with the number of different mutant probes in the various libraries ranging from 2000 to 2,000,000 have been generated using the methods described in U.S. Pat. No. 7,601,510, incorporated herein by reference. In these libraries the single cysteine residue was introduced at one of the sites from the group M21, I23, N24, V25, V26, K27, R28, K29, L30, G31, F55, D74, A73 or T76. Mutant probes from these libraries reveal high degrees of sensitivity and specificity for different FFAu and reveal high degrees of labeling homogeneity and labeling stoichiometry. Two sets of examples from two such libraries are shown in FIG. 5 to illustrate the diversity of possible probes. In this example of screening for mutant probes FFA were added as complexes with albumin to clamp the levels of FFAu.

Example 4

Figure 6B:
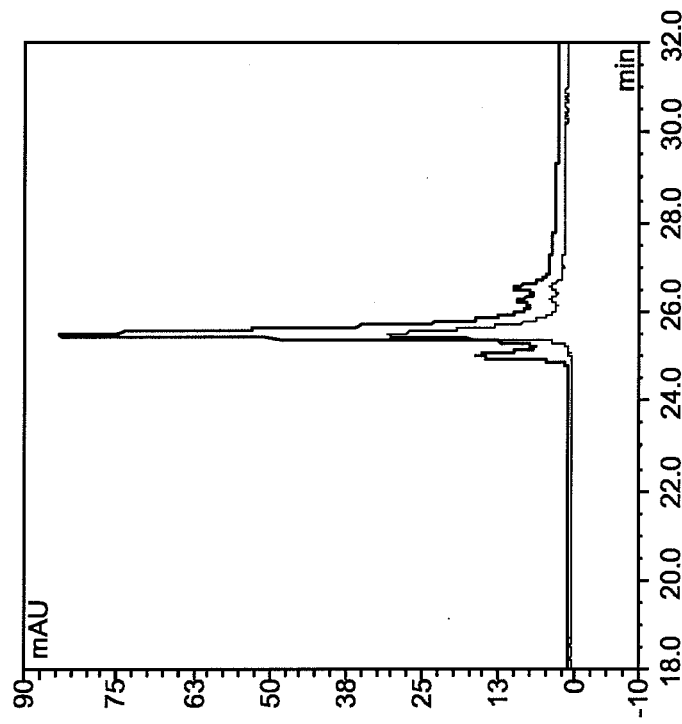
FIG. 6 shows HPLC chromatograms comparing probes without and with 14 surface accessible lysines mutated to arginine. Two examples of these probes are shown in which the probes retain the full complement of their surface lysine side chains (FIGS. 6A, 6C) and the corresponding probes in which 14 surface lysines were mutated to arginine (FIGS. 6B, 6D). The original probes reveal significant multiple site labeling whereas this is markedly reduced to near homogeneity in the KR14 mutants (FIGS. 6B, 6D). As expected, the Ro for the KR14 mutants are significantly smaller and consequently have a larger dynamic range than the original probes. The upper trace in each panel reflects the protein's 280 nm absorbance and the lower trace the acrylodan absorbance at 375 nm.
Figure 6A:
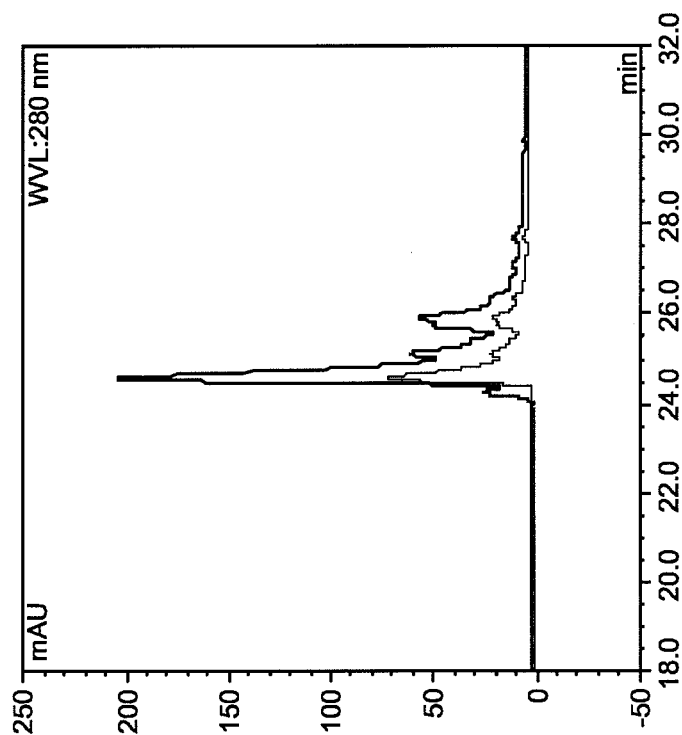

A second approach was developed to obtain homogeneous labeling while retaining the probe response characteristics. In this method surface accessible lysine side chains other than that at position 27 in SEQ ID NO: 5 were mutated to arginine and such mutants were used as templates from which to generate libraries in which additional mutations were introduced in the binding site and/or the helical cap of the iLBP proteins. An important characteristic of the surface lysine to arginine mutations at positions 7, 16, 20, 29, 37, 46, 50, 88, 92, 94, 100, 125, 129, 130 of SEQ ID NO:5 is that they do not significantly affect the binding affinity and specificity of the probes. Moreover, the fluorescence of acrylodan labels at most surface sites is not responsive to FFAu binding. However this fluorescence generally contributes relatively weak fluorescence in the red portion of the acrylodan spectrum. Therefore the Ro value is larger when the surface lysine sites are labeled than in their absence. Two examples of the HPLC traces of probes in which the surface lysines are present and are removed by mutating 14 such lysines to arginine are shown in FIG. 6. These results reveal significant multiple site labeling in the original probes and markedly reduced additional labeling in the KR14 versions. As expected, the Ro for the KR14 mutants are significantly, more than two fold, smaller and consequently these KR14 probes have a larger dynamic range than the original probes. Moreover these palmitate specific probes have virtually identical binding affinities and FFAu profiles.

Example 5

Many labeling sites respond to analyte binding but without the necessary spectral shift to yield a ratio probe (for example the K27C mutant of SEQ NO:2). Because such fluorescent proteins may have other valuable characteristics it would be important to be able to convert such fluorescent proteins into probes, i.e. so that they respond to analyte binding by a change in ratio. This can be accomplished by introducing a second but different fluorophore at a different site so that either the fluorescence of the second fluorophore is insensitive or responds differently to analyte binding. In addition, the fluorescence index of second fluorophore should be measured at a distinct wavelength from the first fluorophore. Examples of such dual fluorophore probes are shown in FIG. 7. The first example involves the bilirubin specific fluorescent protein L2P14F7 (the M18G,G31M mutation of SEQ ID NO 4) which is normally labeled with acrylodan at lysine 27. To convert this to a fluorescence ratio probe, site specific mutagenesis was used to generate a new mutein (L2P14F7-MGCFD) in which the N-terminal alanine residue of the mature L2P14F7 mutein was replaced with glycine-cysteine. Thus, the N-terminus of the mature L2P14F7-MGCFD mutein has the sequence glycine-cysteine-phenylalanine-aspartate instead of alanine-phenylalanine-aspartate, as in the L2P14F7 template. This substitution is designated in the clone name as "MGCFD" and is sometimes described as an "N-terminal MGCFD linker". Then L2P14F7-MGCFD was reacted with Texas Red (TR) maleimide at pH 6 under which conditions only the cysteine was labeled. The L2P14F7-MGCFD-TR after removal of un-reacted TR was reacted with acrylodan at pH 9.3 to label K27. In the second example, the 14 surface lysines of L2P14F7-MGCFD were mutated to arginine and the protein labeled with TR and acrylodan as described above. The resulting probes, L2P14F7-MGCFD-TR-acrylodan and L2P14F7-KR14-MGCFD-TR-acrylodan revealed dual fluorescence at 608 nm (TR) and 525 nm (acrylodan) when excited at 375 nm. As demonstrated in FIG. 7, both probes revealed a ratio (I608/I525) bilirubin binding isotherm response which was well described by single site equilibrium binding with Kds (80 nM) similar to the original L2P14F7. Thus this procedure can effectively convert non-ratio responding fluorescent proteins into probes. In the MGCFD probes the mature (without M) protein has an extra G at the N terminus and therefore in these probes the first residue at position -1 relative to SEQ ID 4.

Example 6

Probes with response profiles that reveal altered specificities to unbound FFA and other unbound analytes, relative to ADIFAB2 and/or other template probes, have been generated by introducing cysteine mutations at positions 21, 23, 24, 25, 26, 27, 28, 29, 30, 31, 55, 74, 73, or 76 of SEQ ID NO: 5 and one or more mutations at positions 11, 14, 17, 18, 21, 23, 31, 34, 36, 38, 40, 47, 49, 51, 53, 55, 60, 62, 68, 70, 72, 73, 74, 78, 80, 82, 89, 91, 93, 102, 104, 106, 113, 115, 117, 119, and 126 of SEQ ID NO: 5. These proteins were labeled with acrylodan at pH 7.0 and the resulting probes revealed homogeneous labeling. Examples of several probes with improved specificity to arachidonate (AA), docosahexanoate (DHA), linoleate (LA), palmitate (PA), palmitoleate (PAO), oleate (OA) and stearate (SA) are shown in Table 1.

TABLE 1

Sequences for specific cysteine labeled Probes and their FFA specificity

| Probe | Specificity | Genotype (SEQ ID 4 mutations) |
|---|---|---|
| L10P7A4-L30C | DHA | 14L 18L 27A 30C 31Y 72A 73L 117A 131D |
| L11P7B3-V26C | SA | 21F 26C 27A 72A 78V 102V 131D |
| L13EP16E11 | OA | 26C 27A 49L 72A 106W 115S 131D |
| L18P5G12-K27C | LA | 14R 18L 27C 73F 117D 131D |
| L19CP10C7 | LA | -1G 1I 14R 18L K27C 71I 73F 117D 131D |
| L50BP4E2 | PA | 18L 21F 23F 27C 31N 72T 73T 74A 76F 131D |
| L50BP9D5 | PA/POA | 18L 21F 23L 27C 31N 72S 73T 74A 76I 117N 131D |
| L61P8B12 | POA | 8I 14L 18L 23L 27Y 30C 31V 53I 55W 72G 74A 78V 82V 91Y 93M 102V 106W 115W 117L 131D |
| L68P3H10 | DHA | 18L 23A 27C 31N 33N 55Q 72W 73T 74L 76I 106A 115E 117V 131D |
| L71AP22B3 | AA | 14W 18L 21I 23L 26C 27A 31N 38V 55S 72W 73T 74S 76P 106A 115E 117V 131D |
| L76P9E4 | OA | 14L 18Y 23T 27L 30C 31I 72G 73I 74A 78V 82P 91S 93M 104F 106L 117L 115A 131D |
| L83P5G8 | MA | -1G 1I 18L 21F 23T 27C 31N 49Q 72T 73T 74A 76V 117H 131D |
| L85P1C2 | LNA | -1G 1I 18L 21L 23Y 27C 31N 72T 73T 74A 76V 117H 128Y 131D |

In L19CP10C7, L83P5G8 and L85P1C2 the mature protein has an extra G at the N terminus and therefore in these probes the first residue at position-1 relative to SEQ ID 4.

Example 7

Probes that reveal reverse response profiles (ΔR<0) and altered specificities to unbound FFA and other unbound analytes, relative to ADIFAB2 and/or other template probes, have been generated by introducing cysteine mutations at positions 21, 23, 24, 25, 26, 27, 28, 29, 30, 31, 55, 74, 73, or 76 of SEQ ID NO: 5 and one or more mutations at positions 11, 14, 17, 18, 21, 23, 31, 34, 36, 38, 40, 47, 49, 51, 53, 55, 60, 62, 68, 70, 72, 73, 74, 78, 80, 82, 89, 91, 93, 102, 104, 106, 113, 115, 117, 119, and 126 of SEQ ID NO: 5. These proteins were labeled with acrylodan at pH 7.0 and the resulting probes revealed homogeneous labeling. Examples of several such probes with cysteine at position 27 and with improved specificity to SA/OA and DHA/AA/EPA are shown in Table 2.

TABLE 2

Examples of cysteine labeled probes that generate a reverse (negative) response and yield FFAu specificity. In addition to the FFA of FIG. 5, the response of these probes to myristate (MA) and vaccinate (VA) is also shown. The fluorescence response for each probe and FFA is the value ΔR/Ro.

| ID | Probe type | AA | LNA | LA | OA | PA | POA | SA | DHA | EPA | MA | VA |
|---|---|---|---|---|---|---|---|---|---|---|---|---|
| L119P4 B11 | SA/OA | −0.25 | −0.34 | −0.54 | −0.87 | −0.74 | −0.35 | −0.90 | −0.17 | −0.15 | −0.20 | −0.61 |
| L119P6 G11 | SA/OA | −0.38 | −0.35 | −0.64 | −0.83 | −0.74 | −0.51 | −0.90 | −0.16 | −0.14 | −0.25 | −0.68 |
| L119P7 F4 | SA/OA | −0.25 | −0.20 | −0.50 | −0.72 | −0.66 | −0.37 | −0.78 | −0.12 | −0.10 | −0.16 | −0.55 |
| L119CP6 B1 | DHA/AA/EPA | −0.57 | −0.33 | −0.34 | −0.38 | −0.27 | −0.16 | −0.32 | −0.58 | −0.47 | −0.06 | −0.28 |
| L79BP4 A11 | DHA/AA/EPA | −0.51 | −0.21 | −0.25 | −0.24 | −0.51 | −0.27 | −0.38 | −0.56 | −0.45 | −0.20 | −0.25 |
| L79BP6 H3 | DHA/AA/EPA | −0.27 | −0.11 | −0.17 | −0.21 | −0.23 | −0.13 | −0.23 | −0.49 | −0.20 | −0.06 | −0.09 |
| L79BP7 G7 | DHA/AA/EPA | −0.48 | −0.22 | −0.25 | −0.22 | −0.49 | −0.25 | −0.36 | −0.67 | −0.47 | −0.17 | −0.22 |
| L79BP8 D7 | DHA/AA/EPA | −0.53 | −0.29 | −0.31 | −0.28 | −0.54 | −0.29 | −0.42 | −0.74 | −0.53 | −0.21 | −0.30 |

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A high throughput method for generating and screening of probes comprising the steps of:
   (a) providing a reference intracellular lipid binding protein (iLBP) comprising a single cysteine residue selected from the group consisting of an iLBP having the sequence set forth in SEQ ID No: 5, L10P7A4-L30C, L11P7B3-V26C, L13EP16E11, L18P5G12-K27C, L19CP10C7, L50BP4E2, L50BP9D5, L61P8B12, L68P3H10, L71AP22B3, L76P9E4, L83P5G8, and L85P1C2, wherein the reference iLBP has a binding specificity for a set of unbound analytes of interest;
   (b) generating polynucleotide mutants encoding a iLBP library comprising an assortment of iLBP muteins of the reference iLBP from a polynucleotide template encoding the reference iLBP;
   (c) expressing the iLBP muteins comprising a single cysteine residue encoded by the library;
   (d) incubating the expressed iLBP muteins with the solid matrix;
   (e) purifying the iLBP muteins by binding to the solid matrix;
   (f) labeling the matrix-bound iLBP muteins with a single fluorophore to produce probes at a pH of less than 8 whereby the fluorophore reacts with the cysteine sidechain and responds to analyte binding by a change in fluorescent ratio at two wavelengths, wherein the fluorophore is covalently attached to the cysteine residue only;
   (g) retrieving the probes with altered specificity to a set of unbound analytes of interest relative to the reference iLBP from the solid matrix;
   (h) screening each of the retrieved probes in a fluorometer in the presence and absence of a set of unbound analytes of interest each with defined unbound concentrations to determine binding of each probe to the set of unbound analytes of interest;
   (i) screening each of the retrieved probes in a fluorometer in the presence and absence of a set of unbound analytes of interest to determine binding of each probe to the set of unbound analytes of interest, wherein the response of the probes differs from the response of the reference labeled iLBP; and
   (j) observing a change in a ratio (R) of a fluorescence index of the probes measured at two different wavelengths in the presence and absence of the unbound analytes.

2. The method of claim 1, wherein the unbound analyte is an unbound metabolite.

3. The method of claim 2, wherein the unbound metabolite is an unbound free fatty acid.

4. The method of claim 1, wherein the iLBP encoded by the template is a Fatty Acid Binding Protein (FABP), or variant thereof that retains the capability of binding an analyte.

5. The method of claim 1, wherein the polynucleotide template encodes iLBP muteins comprising a cleavable or noncleavable affinity tag.

6. The method of claim 5, wherein the polynucleotide template encodes iLBP muteins comprising a poly-histidine affinity tag and the solid matrix comprises an immobilized metal chelate.

7. The method of claim 1, wherein the fluorophore is selected from the group consisting of acrylodan, danzyl aziridine, 4-[N-[(2-iodoacetoxy)ethyl]-N-methylamino]-7-nitrobenz-2-oxa-1,3-diazole ester (IANBDE), and 4-[N-[(2-iodoacetoxy)ethyl]-N-methylamino-7-nitrobenz-2-oxa-1,3-diazole (IANBDA).

8. The method of claim 1, wherein the labeling comprises labeling the matrix-bound iLBP muteins with a first fluorophore and a second fluorophore at two specific sites comprising reacting cysteine with the first fluorophore at pH less than or equal to 8; and reacting lysine with the second fluorophore at pH greater than 8.

9. The method of claim 8, wherein the first fluorophore is selected from the group consisting of acrylodan, danzyl aziridine, 4-[N-[(2-iodoacetoxy)ethyl]-N-methylamino]-7-nitrobenz-2-oxa-1,3-diazole ester (IANBDE), and 4-[N-[(2-iodoacetoxy)ethyl]-N-methylamino-7-nitrobenz-2-oxa-1,3-diazole (IANBDA) and wherein the second fluorophore is selected from the group consisting of Alexa Fluor dyes, Bodipy, fluorescein, rhodamine and Texas Red.

10. The method of claim 1, wherein labeling comprises labeling the matrix-bound iLBP muteins with a first fluorophore and a second fluorophore at two specific sites comprising reacting cysteine with the first fluorophore at pH less than or equal to 8; and reacting the amino terminus of the iLBP mutein with the second fluorophore.

11. The method of claim 1, wherein a second fluorophore is provided by addition of an acceptor protein or peptide domain to each of the iLBP muteins and wherein the protein or peptide domains are then labeled with a second fluorophore of interest.

12. The method of claim 11, wherein the acceptor protein or peptide domain is selected from the group consisting of a bi-functional polypeptide fused to a protein that can be crosslinked to a solid phase (SNAP-Tag®), CLIP-Tag®, or ACP-Tag™) or a biotinylation tag.

13. The method of claim 11, wherein the acceptor protein or peptide domain or the fluorescent protein has zero or a reduced response in intensity and/or wavelength of emitted fluorescence upon binding to the analytes in the set of unbound analytes of interest compared to the fluorescence of the iLBP mutein portion of the probe.

14. The method of claim 1, wherein the analytes are complexed with a carrier macromolecule selected from the group consisting of albumin, lipid binding proteins, lipid vesicles and cyclodextrin, whereby the complex of the analytes and the carrier macromolecule buffers the concentration of the unbound analyte which provides clamping of a level of unbound analyte.

15. The method of claim 14, wherein the carrier macromolecule is albumin.

16. The method of claim 1, wherein the fluorescence index is intensity, polarization and/or lifetime of the probe, in the presence and absence of each analyte in the set of analytes of interest.

17. The method of claim 1, wherein the polynucleotide template encodes an iLBP mutein comprising a cysteine and further comprising substituting all surface accessible lysine residues before associating the iLBP muteins with the fluorophore.

18. The method of claim 1, wherein the polynucleotide template encodes an iLBP mutein comprising a cysteine and further comprising substituting all but one surface accessible lysine residues before associating the iLBP muteins with the fluorophore.

19. The method of claims 17, wherein the surface accessible lysine residues are substituted with arginine or alanine.

20. The method of claim 18, wherein the all but one surface accessible lysine residues are substituted with arginine or alanine.

21. The method of claim 1, further comprising identifying probe characteristics comprising:
determining a value for R by the following formula:

$$R = F\lambda 1 / F\lambda 2$$

wherein $F\lambda 1$ is a measured fluorescence intensity (intensity of a probe with analyte present minus intensity of the analyte without the probe present) at a first emission wavelength, $F\lambda 2$ is a measured fluorescence intensity (intensity of a probe with analyte present minus intensity of the analyte without the probe present) at a second emission wavelength;
measuring the difference between R in the presence and absence of the analyte by the formula $$\Delta R = R_{+analyte} - R_0$$

wherein $R_{+analyte}$ is the ratio value for the measurement done in the presence of the analyte and $R_0$ is the ratio value for the measurement done in the absence of the analyte; and
comparing $\Delta R$ for the probe to $\Delta R_{reference}$ for a standard.

22. The method of claim 21, wherein the standard is the fluorescent probe made from the protein encoded by the polynucleotide template used to generate mutations for the high throughput screening.

23. The method of claim 21, wherein the standard is acrylodan labeled rat intestinal fatty acid binding protein (ADIFAB) or acrylodan labeled Leu72 to Ala mutant of the rat intestinal fatty acid binding protein (ADIFAB2).

24. The method of claim 21, wherein probes are screened with n unbound analytes and a probe is found for which *$\Delta R$*/$\Delta R$reference, where *$\Delta R$* is the absolute value of $\Delta R$, is largest and >0.1 for one or more of the n unbound molecules and is at least 0.1 smaller for the remaining unbound molecules.

25. The method of claim 24, wherein the unbound analytes are unbound metabolites.

26. The method of claim 25, wherein the unbound metabolites are unbound fatty acids.

27. The method of claim 11, wherein the acceptor protein or peptide domain or the fluorescent protein has zero or a significantly reduced response in intensity and/or wavelength of emitted fluorescence upon binding to the analytes in the set of unbound analytes of interest compared to the fluorescence of the iLBP mutein portion of the probe.

* * * * *

UNITED STATES PATENT AND TRADEMARK OFFICE
CERTIFICATE OF CORRECTION

| | |
|---|---|
| PATENT NO. | : 9,134,317 B2 |
| APPLICATION NO. | : 12/810505 |
| DATED | : September 15, 2015 |
| INVENTOR(S) | : Alan Marc Kleinfeld et al. |

It is certified that error appears in the above-identified patent and that said Letters Patent is hereby corrected as shown below:

In the Specification

In column 1 at line 7 (approx.), Change "This application" to --This application is the U.S. National Phase under 35 U.S.C. § 371 of International Application PCT/US2009/031341, filed January 16, 2009, which--.

In column at lines 8-9 (approx.), Change "2008, which is incorporated herein by reference" to --2008.--.

In column 2 at line 24, Change "eiconsanoids," to --eicosanoids,--.

In column 6 at line 48, Change "(ADIFAB)" to --ADIFAB--.

In column 6 at line 49, Change "(ADIFAB2)." to --ADIFAB2.--.

In column 7 at line 36, Change "iLPP" to --iLBP--.

In column 8 at lines 11-12, Change "eicosapentaenoate_(EPA)," to --eicosapentaenoate (EPA),--.

In column 10 at line 37, Change "construction" to --construction.--.

In column 16 at line 8 (approx.), Change "determined" to --determined.--.

In columns 23-24 at line 33 (approx.), Change "subsitition." to --substitution.--.

In columns 25-26 at line 9 (approx.), Change "subsitition." to --substitution.--.

In the Claims

In column 25 at line 55 (approx.), In Claim 1, change "with the" to --with a--.

In column 27 at line 30 (approx.), In Claim 12, change "(SNAP-Tag®)," to --(SNAP-Tag®,--.

In column 28 at line 4 (approx.), In Claim 19, change "claims" to --claim--.

In column 28 at line 30 (approx.), In Claim 21, change "AR" to --ΔR--.

Signed and Sealed this
Tenth Day of May, 2016

Michelle K. Lee
*Director of the United States Patent and Trademark Office*

SEQUENCE LISTING

<160> NUMBER OF SEQ ID NOS: 5

<210> SEQ ID NO 1
<211> LENGTH: 399
<212> TYPE: DNA
<213> ORGANISM: Rattus norvegicus
<220> FEATURE:
<221> NAME/KEY: CDS
<222> LOCATION: (1)...(399)
<223> OTHER INFORMATION: wild-type rat intestinal fatty acid binding protein cDNA sequence

<400> SEQUENCE: 1

```
atg gca ttt gat ggc act tgg aaa gta tac cgg aat gag aac tat gaa      48
Met Ala Phe Asp Gly Thr Trp Lys Val Tyr Arg Asn Glu Asn Tyr Glu
 1               5                  10                  15 aag ttc atg gag aaa atg ggc att aac gtg gtg aag agg aag ctt gga      96
Lys Phe Met Glu Lys Met Gly Ile Asn Val Val Lys Arg Lys Leu Gly
             20                  25                  30 gct cat gac aac ttg aaa ctg acg atc aca cag gaa gga aat aaa ttc     144
Ala His Asp Asn Leu Lys Leu Thr Ile Thr Gln Glu Gly Asn Lys Phe
         35                  40                  45 aca gtc aaa gaa tca agc aac ttc cga aac att gat gtt gtg ttt gaa     192
Thr Val Lys Glu Ser Ser Asn Phe Arg Asn Ile Asp Val Val Phe Glu
     50                  55                  60 ctc ggc gtc gac ttt gcc tat agt cta gca gat gga aca gaa ctc act     240
Leu Gly Val Asp Phe Ala Tyr Ser Leu Ala Asp Gly Thr Glu Leu Thr
 65                  70                  75                  80 ggg acc ttg acc atg gag gga aat aaa ctt gtt gga aaa ttc aaa cgt     288
Gly Thr Leu Thr Met Glu Gly Asn Lys Leu Val Gly Lys Phe Lys Arg
                 85                  90                  95 gta gac aat gga aag gag ctg att gct gtc cga gag att tct ggt aac     336
Val Asp Asn Gly Lys Glu Leu Ile Ala Val Arg Glu Ile Ser Gly Asn
            100                 105                 110 gaa cta atc caa acc tac aca tat gaa gga gtg gag gcc aag cgc atc     384
Glu Leu Ile Gln Thr Tyr Thr Tyr Glu Gly Val Glu Ala Lys Arg Ile
        115                 120                 125 ttt aag aag gaa tag                                                 399
Phe Lys Lys Glu
    130
```

<210> SEQ ID NO 2
<211> LENGTH: 131
<212> TYPE: PRT
<213> ORGANISM: Rattus norvegicus
<220> FEATURE:
<221> NAME/KEY: PEPTIDE
<222> LOCATION: (1)...(131)
<223> OTHER INFORMATION: wild-type rat intestinal fatty acid binding protein
<220> FEATURE:
<221> NAME/KEY: ACETYLATION
<222> LOCATION: (1)...(1)

<400> SEQUENCE: 2

```
Ala Phe Asp Gly Thr Trp Lys Val Asp Arg Asn Glu Asn Tyr Glu Lys
 1               5                  10                  15

Phe Met Glu Lys Met Gly Ile Asn Val Val Lys Arg Lys Leu Gly Ala
             20                  25                  30

His Asp Asn Leu Lys Leu Thr Ile Thr Gln Glu Gly Asn Lys Phe Thr
         35                  40                  45

Val Lys Glu Ser Ser Asn Phe Arg Asn Ile Asp Val Val Phe Glu Leu
     50                  55                  60

Gly Val Asp Phe Ala Tyr Ser Leu Ala Asp Gly Thr Glu Leu Thr Gly
 65                  70                  75                  80

Thr Trp Thr Met Glu Gly Asn Lys Leu Val Gly Lys Phe Lys Arg Val
                 85                  90                  95

Asp Asn Gly Lys Glu Leu Ile Ala Val Arg Glu Ile Ser Gly Asn Glu
            100                 105                 110

Leu Ile Gln Thr Tyr Thr Tyr Glu Gly Val Glu Ala Lys Arg Ile Phe
        115                 120                 125
```

Lys Lys Glu
    130

<210> SEQ ID NO 3
<211> LENGTH: 426
<212> TYPE: DNA
<213> ORGANISM: Rattus norvegicus
<220> FEATURE:
<221> NAME/KEY: mutation
<222> LOCATION: (1)...(426)
<223> OTHER INFORMATION: rat intestinal fatty acid binding protein DNA
      sequence coding for substitution of alanine for
      leucine at position 72
<220> FEATURE:
<223> OTHER INFORMATION: 3' terminus codes for a 6his tag

<400> SEQUENCE: 3

```
atggcatttg atggcacttg gaaagtagac cggaatgaga actatgaaaa gttcatggag    60
aaaatgggca ttaacgtggt gaagaggaag cttggagctc atgacaactt gaaactgacg   120
atcacacagg aaggaaataa attcacagtc aaagaatcaa gcaacttccg aaacattgat   180
gttgtgtttg aactcggcgt cgactttgcc tatagtgctg cagatggaac agaactcacc   240
ggtacctgga caatgGaggg aaataaactt gttggaaagt ttaaacgtgt agacaatgga   300
aaggagctga ttgctgtccg agagatttct ggtaacgaac taatccagac ctacacatat   360
gaaggagtgg aggccaagcg gatctttaag aaggaccgcg gtcatcatca ccatcatcac   420
tagtaa                                                              426
```

<210> SEQ ID NO 4
<211> LENGTH: 139
<212> TYPE: PRT
<213> ORGANISM: Rattus norvegicus
<220> FEATURE:
<221> NAME/KEY: MUTAGEN
<222> LOCATION: (72)...(72)
<223> OTHER INFORMATION: rat intestinal fatty acid binding protein with
      alanine substitution for leucine at position 72 and Glu 131 to Asp
      subsitition.
<220> FEATURE:
<223> OTHER INFORMATION: COOH-terminal affinity tag comprising Arg132,
      Gly133 and 6 histidines

<400> SEQUENCE: 4

Ala Phe Asp Gly Thr Trp Lys Val Asp Arg Asn Glu Asn Tyr Glu Lys
 1               5                  10                  15

Phe Met Glu Lys Met Gly Ile Asn Val Val Lys Arg Lys Leu Gly Ala
            20                  25                  30

His Asp Asn Leu Lys Leu Thr Ile Thr Gln Glu Gly Asn Lys Phe Thr
        35                  40                  45

Val Lys Glu Ser Ser Asn Phe Arg Asn Ile Asp Val Val Phe Glu Leu
    50                  55                  60

Gly Val Asp Phe Ala Tyr Ser Ala Ala Asp Gly Thr Glu Leu Thr Gly
65                  70                  75                  80

Thr Trp Thr Met Glu Gly Asn Lys Leu Val Gly Lys Phe Lys Arg Val
                85                  90                  95

Asp Asn Gly Lys Glu Leu Ile Ala Val Arg Glu Ile Ser Gly Asn Glu
            100                 105                 110

Leu Ile Gln Thr Tyr Thr Tyr Glu Gly Val Glu Ala Lys Arg Ile Phe
        115                 120                 125

Lys Lys Asp Arg Gly His His His His His
    130                 135

```
<210> SEQ ID NO 5
<211> LENGTH: 139
<212> TYPE: PRT
<213> ORGANISM: Rattus norvegicus
<220> FEATURE:
<221> NAME/KEY: MUTAGEN
<222> LOCATION: (131)...(131)
<223> OTHER INFORMATION: rat intestinal fatty acid binding protein with
      Glu 131 to Asp subsitition.
<220> FEATURE:
<223> OTHER INFORMATION: COOH-terminal affinity tag comprising Arg132,
      Gly133 and 6 histidines

<400> SEQUENCE: 5

Ala Phe Asp Gly Thr Trp Lys Val Asp Arg Asn Glu Asn Tyr Glu Lys
 1               5                  10                  15

Phe Met Glu Lys Met Gly Ile Asn Val Val Lys Arg Lys Leu Gly Ala
            20                  25                  30

His Asp Asn Leu Lys Leu Thr Ile Thr Gln Glu Gly Asn Lys Phe Thr
        35                  40                  45

Val Lys Glu Ser Ser Asn Phe Arg Asn Ile Asp Val Val Phe Glu Leu
    50                  55                  60

Gly Val Asp Phe Ala Tyr Ser Leu Ala Asp Gly Thr Glu Leu Thr Gly
65                  70                  75                  80

Thr Trp Thr Met Glu Gly Asn Lys Leu Val Gly Lys Phe Lys Arg Val
                85                  90                  95

Asp Asn Gly Lys Glu Leu Ile Ala Val Arg Glu Ile Ser Gly Asn Glu
            100                 105                 110

Leu Ile Gln Thr Tyr Thr Tyr Glu Gly Val Glu Ala Lys Arg Ile Phe
        115                 120                 125

Lys Lys Asp Arg Gly His His His His His His
    130                 135
```